(12) United States Patent
Hare et al.

(10) Patent No.: US 9,746,457 B2
(45) Date of Patent: Aug. 29, 2017

(54) CARDIAC STEM CELLS AND METHODS OF IDENTIFYING AND USING THE SAME

(71) Applicant: VESTION, INC., Miami, FL (US)

(72) Inventors: Joshua Hare, Miami Beach, FL (US); Konstantinos Chatzistergos, Miami Beach, FL (US)

(73) Assignee: Vestion, Inc., Miami, FL (US)

( * ) Notice: Subject to any disclaimer, the term of this patent is extended or adjusted under 35 U.S.C. 154(b) by 0 days.

(21) Appl. No.: 14/648,621

(22) PCT Filed: Dec. 2, 2013

(86) PCT No.: PCT/US2013/072660
§ 371 (c)(1),
(2) Date: May 29, 2015

(87) PCT Pub. No.: WO2014/093051
PCT Pub. Date: Jun. 19, 2014

(65) Prior Publication Data
US 2015/0316535 A1 Nov. 5, 2015

Related U.S. Application Data

(60) Provisional application No. 61/731,835, filed on Nov. 30, 2012.

(51) Int. Cl.
| | |
|---|---|
| G01N 33/50 | (2006.01) |
| A61K 35/34 | (2015.01) |
| C12N 5/077 | (2010.01) |
| A61K 45/06 | (2006.01) |
| C12N 5/0775 | (2010.01) |

(52) U.S. Cl.
CPC ......... G01N 33/5005 (2013.01); A61K 35/34 (2013.01); A61K 45/06 (2013.01); C12N 5/0657 (2013.01); C12N 5/0662 (2013.01); G01N 33/5073 (2013.01); C12N 2506/02 (2013.01)

(58) Field of Classification Search
None
See application file for complete search history.

(56) References Cited

U.S. PATENT DOCUMENTS

| | | | |
|---|---|---|---|
| 6,387,369 B1 | 5/2002 | Pittenger et al. | |
| 6,930,222 B2 | 8/2005 | Yu | |
| 7,070,943 B2 * | 7/2006 | Darzynkiewicz .. | G01N 33/5011 435/6.13 |
| 2003/0054973 A1 | 3/2003 | Anversa | |
| 2004/0126879 A1 | 7/2004 | Schneider et al. | |
| 2006/0008450 A1 | 1/2006 | Verfaillie et al. | |
| 2007/0005389 A1 | 1/2007 | Apparao et al. | |
| 2011/0123500 A1 | 5/2011 | Anversa et al. | |
| 2012/0034595 A1 | 2/2012 | Phillips et al. | |

FOREIGN PATENT DOCUMENTS

| | | |
|---|---|---|
| WO | WO00/06701 A1 | 2/2000 |
| WO | WO2006/039630 A2 | 4/2006 |
| WO | WO2006/039630 A3 | 4/2006 |
| WO | WO2008/054819 A2 | 5/2008 |
| WO | WO2008/058216 A2 | 5/2008 |
| WO | WO2014/093051 A2 | 6/2014 |

OTHER PUBLICATIONS

Beltrami et al., Adult Cardiac Stem Cells Are Multipotent and Support Myocardial Regeneration, Cell (Sep. 19, 2003), (114) pp. 763-776.
Dai et al., "Allogeneic Mesenchymal Stem Cell Transplantation in Postinfarcted Rat Myocardium Short- and Long-Term Effects," Circulation, Lippincott Williams & Wilkins, U.S. (Jul. 12, 2005), 112(2) pp. 214-223.
Dingar et al., "Anti-apoptotic Function of the E2F Transcription Factor 4 (E2F4)/p130, a Member of Retinoblastoma Gene Family in Cardiac Myocytes", Journal of Molecular and Cellular Cardiology (Sep. 15, 2012), 53(6):820-828.
European Patent Office, "Extended European Search Report" mailed Feb. 24, 2012, pp. 1-13.
European Patent Office, "Extended European Search Report" , mailed Mar. 16, 2016, pp. 1-10.
Hatzistergos et al., "Bone Marrow Mesenchymal Stem Cells Stimulate Cardiac Stem Cell Proliferation and Differentiation", Circulation Research (Oct. 1, 2010), 107(7):913-922.
Hou et al., "Transplantation of mesenchymal stem cells from human bone marrow improves damaged heart function in rats," International Journal of Cardiology, Elsevier Science Publishers (Jan. 25, 2007) 115(2) pp. 220-228.
Huang et al., "Transplantation of angiogenin-overexpressing mesenchymal stem cells synergistically augments cardiac function in a porcine model of chronic ischemia," Journal of Thoracic and Cardiovascular Surgery, Mosby-Yearbook Inc. (Nov. 29, 2006), 132(6) pp. 1329-1338.
Jiang et al., "Homing and differentiation of mesenchymal stem cells delivered intravenously to ischemic myocardium in vivo: a times-series study," Pflugers Archiv—European Journal of Physiology (Aug. 17, 2006), 453(1) pp. 43-52.
Li et al., "Bone marrow mesenchymal stem cells differentiate into cardiac phenotypes by cardiac microenvironment", Journal of Molecular and Cellular Cardiology, Academic Press, GB (Jan. 24, 2007), 42(2) pp. 295-303.
Sdek et al., "Assessment of Cardiomyocyte DNA Synthesis During Hypertrophy in Adult Mice", The Journal of Cell Biology: JCB (Aug. 8, 2011), 266(3):H1439-423.

(Continued)

*Primary Examiner* — Daniel C Gamett
(74) *Attorney, Agent, or Firm* — Pepper Hamilton LLP

(57) ABSTRACT

Methods of isolating cardiac cells, including cardiac cells capable of regenerating cardiac tissue are provided. Compositions comprising cardiac cells, including cardiac cells capable of regenerating cardiac tissue are also provided. Methods of using cardiac cells, cardiac progenitor cells, including cardiac cells capable of regenerating cardiac tissue, are provided. Methods of identifying the prognosis of patients treated for heart disease and/or methods of predicting the regeneration of cardiac cells in a subject are also provided.

14 Claims, 15 Drawing Sheets

(56) References Cited

OTHER PUBLICATIONS

Toma et al., "Human Mesenchymal Stem Cells Differentiate to a Cardiomyocyte Phenotype in the Adult Murine Heart," Circulation, Lippincott Williams & Wilkins (Jan. 8, 2002), 105(1) pp. 93-98.
Uosaki et al., "Direct Contact with Endoderm-Like Cells Efficiently Induces Cardiac Progenitors from Mouse and Human Pluripotent Stem Cells", Plos One (Oct. 1, 2012), 7(10):e46413.
Wang et al. "The roles of mesenchymal stem cells (MSCs) therapy in ischemic heart diseases," Biochemical and Biophysical Research Communications, Academic Press Inc. (Jun. 9, 2007), 359(2) pp. 189-193.
International Search Report and Written Opinion for International Application No. PCT/US2013/072660 mailed Jul. 1, 2014.
Hatzistergos et al., Abstract 19546: Retinoblastoma Regulates Cardiac and Mesenchymal Stem Cell Niches during Adult Heart Regeneration, *Circulation* (Nov. 20, 2012), 126:A19546.
Yang et al., A Key Role for Telomerase Reverse Transcriptase Unit in Modulating Human Embryonic Stem Cell Proliferation, Cell Cycle Dynamics, and In Vitro Differentiation, *Stem Cells* (Jan. 17, 2008), 26(4):805-863.
Chatzistergos et al., "Abstract 18448: Ckit Marks Cardiac Neural Crest Progenitors in the Developing Mouse Heart," American Heart Association, Scientific Sessions and Resuscitation Science Symposium (2013), 128(22) pp. 1-20.
International Search Report and Written Opinion for International Application No. PCT/US2014/062939 mailed Mar. 16, 2015.
Tamura et al., "Neural Crest-Derived Stem Cells Migrate and Differentiate Into Cardiomyocytes After Myocardial Infarction," Arterioscler Thromb Vasc Biol. (2011), 31(3) pp. 582-589.
Tomita et al., Cardiac neural crest cells contribute to the dormant multipotent stem cell in the mammalian heart, J Cell Biology (2005), 170(7) pp. 1135-1146.

\* cited by examiner

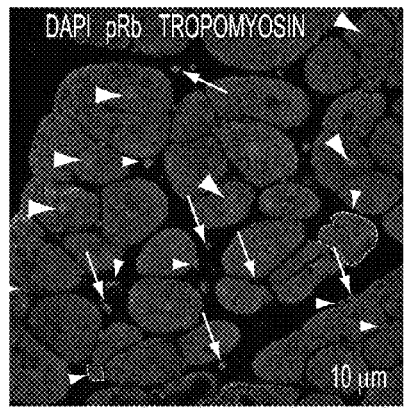
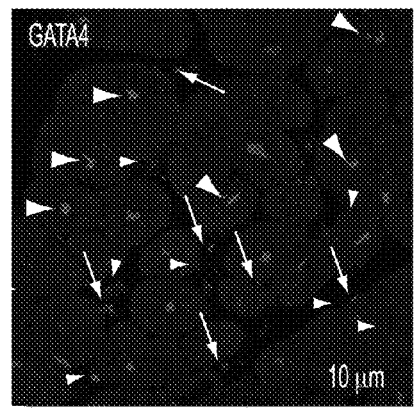
FIG. 1A  FIG. 1B
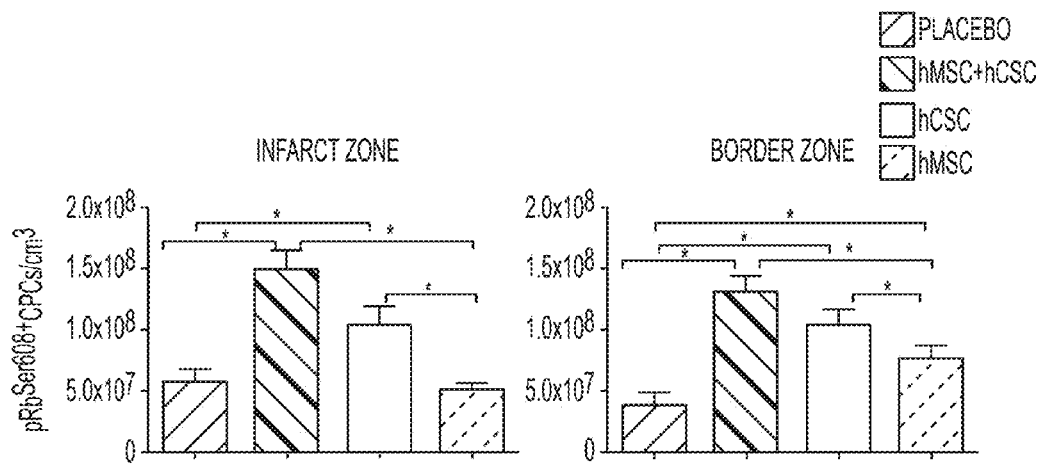
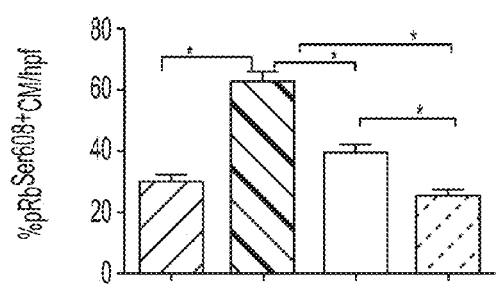
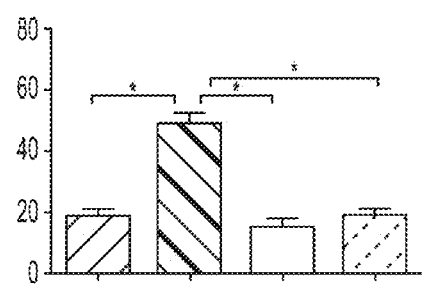
FIG. 1C  FIG. 1D
FIG. 1E  FIG. 1F

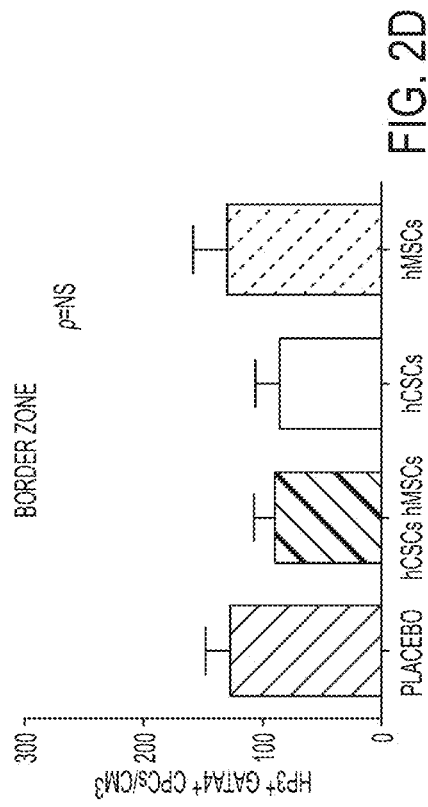
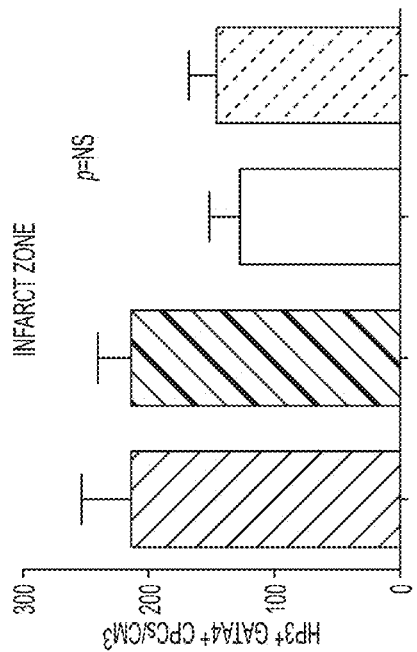
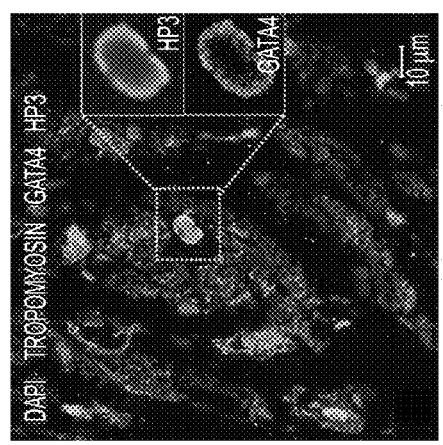
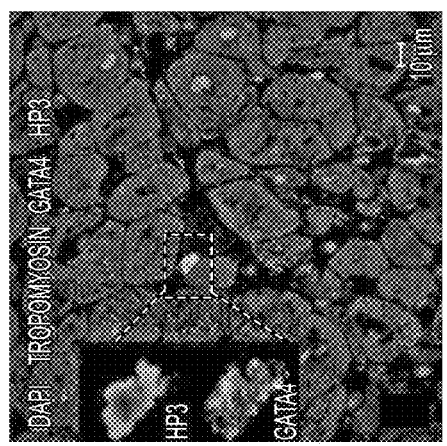

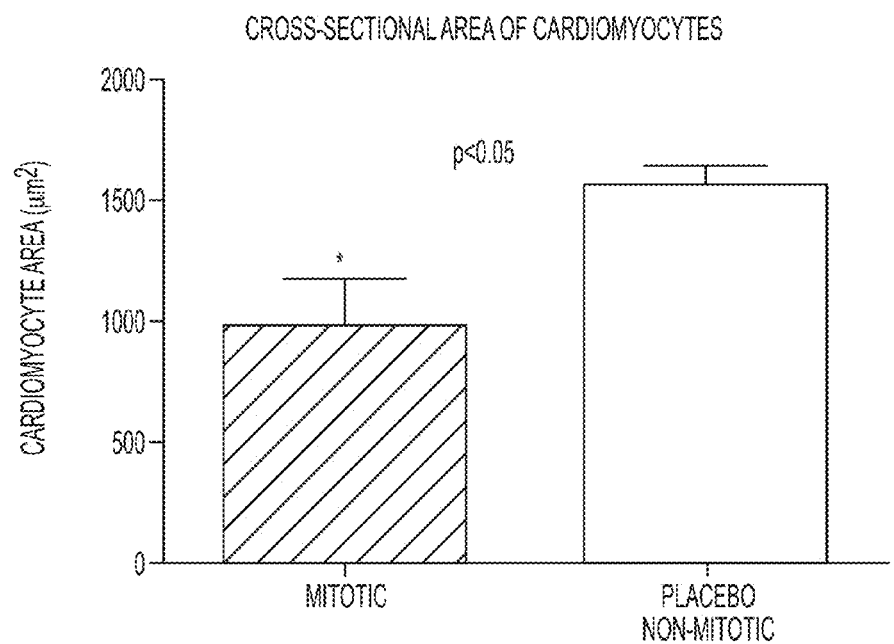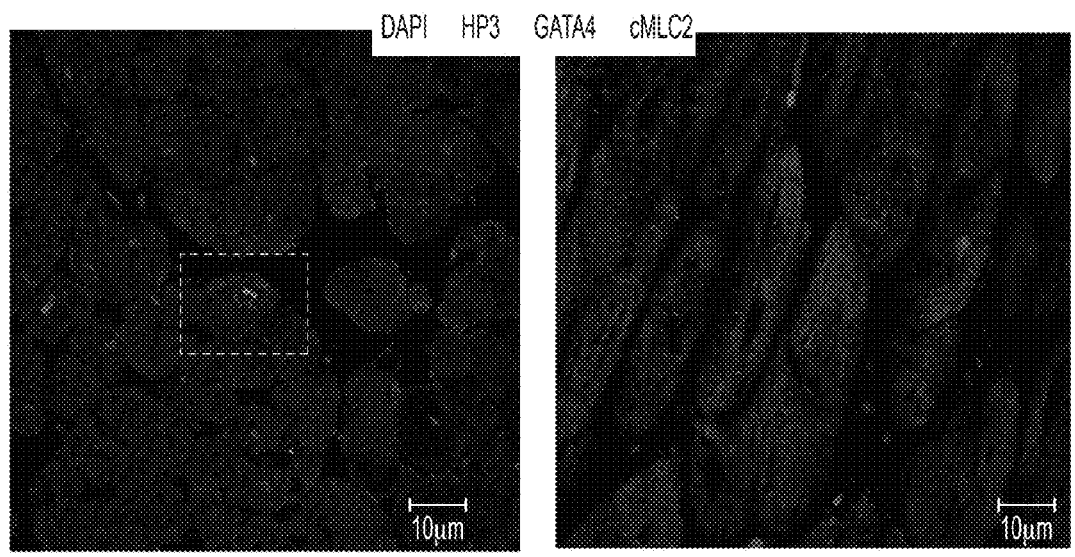
FIG. 7

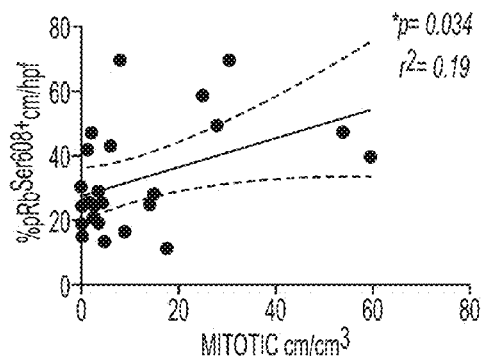 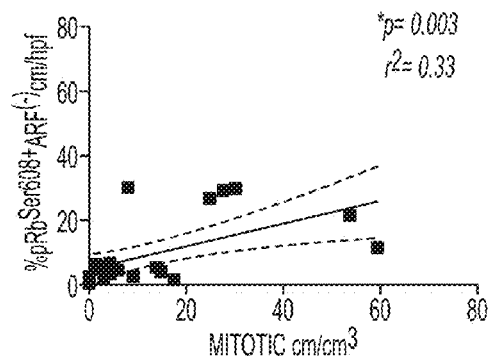
FIG. 8A  FIG. 8B
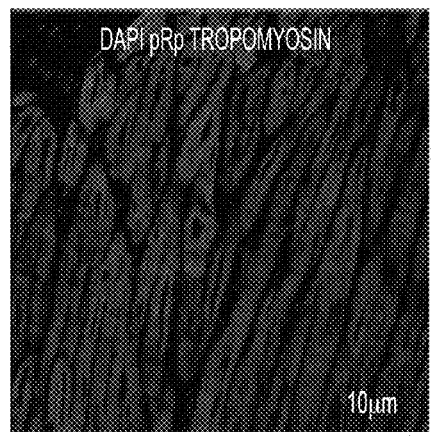 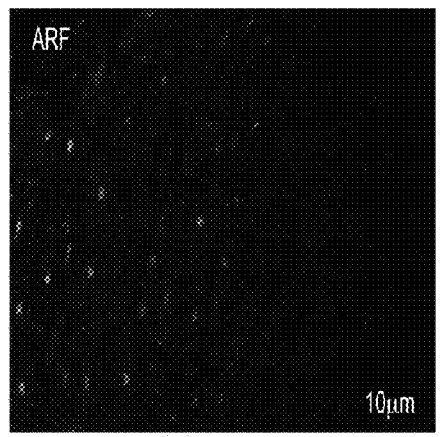
FIG. 9A  FIG. 9B
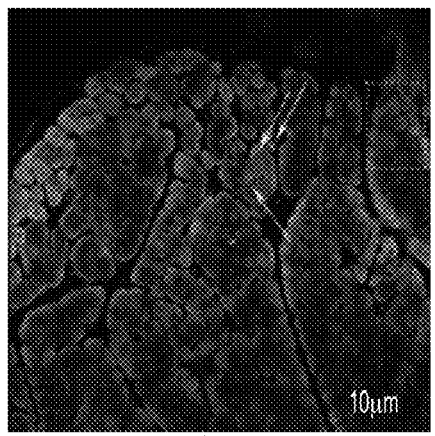 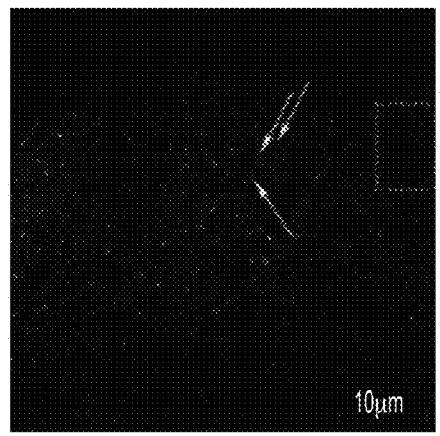
FIG. 9C  FIG. 9D

CARDIAC STEM CELLS AND METHODS OF IDENTIFYING AND USING THE SAME

CROSS-REFERENCE TO RELATED APPLICATIONS

This application is a 35 U.S.C. §371 national phase application of PCT Application No. PCT/US2013/072660, filed Dec. 2, 2013, which claims priority to U.S. Provisional application Ser. No. 61/731,835, filed on Nov. 30, 2012, each of which is hereby incorporated by reference in its entirety.

GOVERNMENT INTERESTS

The embodiments disclosed herein were made with government support under P20 HL101443, awarded by US National Institutes of Health, therefore, the government may have certain rights.

BACKGROUND

Not Applicable

BRIEF SUMMARY OF THE INVENTION

This Summary is provided to present a summary of some of the embodiments described herein. This summary is submitted with the understanding that it will not be used to interpret or limit the scope or meaning of the claims.

Embodiments described herein are directed to marker compositions predictive of cardiac regeneration following therapy. Methods of monitoring patient recovery, mitosis, drug discovery and the like are also provided. In some embodiments, the methods utilize detection of biomarker expression, activity or function. Novel cell types and uses thereof, are also provided.

Disclosed herein are compositions and methods to isolate cardiac progenitor cells, and methods to treat a subject for a heart disease. Some embodiments disclosed herein are methods of predicting regeneration of cardiac cells. In some embodiments, a method of predicting regeneration of cardiac cells in a subject treated for a heart disease may comprise obtaining a biological sample comprising cardiac cells from the subject; measuring phosphorylated retinoblastoma (pRb) levels in the biological sample; and comparing the phosphorylated retinoblastoma (pRb) levels in the biological sample to a baseline control, wherein an increased levels of pRb levels in the subject's biological sample when compared to the baseline control is predictive of the regeneration of the cardiac cells in the subject.

Some embodiments disclosed herein are directed to identify prognosis of a subject treated for heart disease. In some embodiments, a method of identifying a subject treated for heart disease as a subject with a good prognosis may comprise obtaining a biological sample comprising cardiac cells from the subject; measuring phosphorylated retinoblastoma (pRb) levels in the biological sample; and comparing the phosphorylated retinoblastoma (pRb) levels in the biological sample to a baseline control, wherein an increased level of pRb in the subject's biological sample when compared to the baseline control identifies that subject as having a good prognosis. In some embodiments, the subject may be treated with adult bone marrow-derived mesenchymal cells (MSCs), adult cardiac stem cells (CSCs), or any combination thereof.

Some embodiments are directed to identifying candidate agents that modulate Rb pathway. In some embodiments, a method of identifying a candidate agent to modulate Rb pathway in a cardiac progenitor cell may comprise contacting the candidate agent with a population of cardiac progenitor cells (CPCs); and comparing phosphorylated Rb levels in the population of cardiac progenitor cells contacted with the candidate agent to phosphorylated Rb levels in a population of CPCs not contacted with the candidate agent, wherein a difference in the phosphorylated Rb levels identifies the candidate agent as an agent that modulates the Rb pathway in the cardiac progenitor cell. In some embodiments, the cardiac progenitor cells (CPCs) are positive for phosphorylated $Rb^{ser608}$ ($pRb^{ser608}$), Gata4, or any combination thereof. In some embodiments, the difference in the phosphorylated Rb levels is at least 10%.

In some embodiments, a method of regenerating cardiac cells in vitro or in vivo may comprise contacting the cardiac cells with at least one agent that inhibits the function of retinoblastoma (Rb), alternate reading frame of Ink4a (ARF) protein, or any combination thereof. The cardiac cells may be cardiac stem cells (CSCs), cardiac progenitor cells (CPCs), cardiomyocytes, or any combination thereof. In some embodiments, the agent may be a siRNA inhibitor, a shRNA inhibitor, an antisense nucleotide inhibitor, a peptide mimetic inhibitor, a small molecule, an antibody, a kinase that phosphorylates Rb, a transcriptional repressor of ARF, or any combination thereof. In some embodiments, the agent may increase the phosphorylation of Rb in cardiac cells, and/or decrease the expression of ARF in cardiac cells.

In other embodiments, a method of treating an ischemic disorder in a subject in need thereof may comprise administering a therapeutically effective amount of an agent that inhibits the function of retinoblastoma (Rb) and/or alternate reading frame of Ink4a (ARF) in cardiac cells. The ischemic disorder may be caused by heart surgery, organ transplantation, angioplasty, stenting, or any combination thereof. In some embodiments, the agent may increase the phosphorylation of Rb in cardiac cells, decrease the expression of ARF in cardiac cells, or any combination thereof.

In a further embodiment, a progenitor cell may be formed by the process of co-culturing mesenchymal stem cells (MSCs) and cardiac stem cells (CSCs) in vitro or in vivo, wherein the progenitor cell comprises a phenotype identified by markers positive for phosphorylated retinoblastoma serine 608 ($pRb^{ser608}$), and Gata4 ($Gata4^+$). In some embodiments, the progenitor cell may be ARF negative. In other embodiments, the progenitor cell may be a cardiac progenitor cell (CPC).

Disclosed herein are methods to identify cardiac precursor cells. In some embodiments, a method of isolating cardiac progenitor cells from a population of cardiac cells may comprise identifying the cardiac progenitor cells in the population as cells comprising phosphorylated retinoblastoma protein; and isolating the identified cardiac progenitor cells. In some embodiments, the cardiac progenitor cells are identified by contacting the population of cardiac cells with an agent that detects phosphorylated Rb. In some embodiments, the agent that detects the phosphorylated Rb may be an antibody. In some embodiments, the method may further comprise administering the isolated cardiac progenitor cells in a therapeutically effective amount to a subject in need of such administration. In some embodiments, the subject may be a subject with a heart disease.

In some embodiments, a method of isolating cardiac progenitor cells from a population of cardiac cells may comprise identifying the cardiac progenitor cells in the population as cells that are positive for at least one marker selected from phospho-Rb$^{pos}$, Gata4$^{pos}$, ARF$^{neg}$, and any combination thereof; and isolating the identified cardiac progenitor cells. In some embodiments, the isolated cardiac progenitor cells may have the following markers: N-cadherin$^{pos}$, connexin-43$^{pos}$, Isl1$^{pos}$, Wt1$^{pos}$, CDK2$^{pos}$, CDK4$^{pos}$, CDK6$^{pos}$, E2F$^{pos}$, phospho-p107$^{pos}$, phospho-p130$^{pos}$, CCNA$^{pos}$, CCND1$^{pos}$, CCND2$^{pos}$, CCND3$^{pos}$, CCNE$^{pos}$, c-kit$^{pos}$, CD3$^{neg}$, CD14$^{neg}$, CD68$^{neg}$, Nkx2.5$^{pos}$, MITF$^{pos}$, MEF2$^{pos}$, and any combination thereof. In an additional embodiment, a composition may comprise an isolated population of cardiac progenitor cells obtained according to the methods described herein.

In some embodiments, a method of isolating regenerative cardiomyocytes from a population of mature cardiomyocytes may comprise identifying the regenerative cardiomyocytes in the population as cells that are positive for at least one marker selected from phospho-Rb$^{pos}$, Gata4$^{pos}$, ARF$^{neg}$, N-cadherin$^{pos}$, connexin-43$^{pos}$, Isl1$^{pos}$, Wt1$^{pos}$, CDK2$^{pos}$, CDK4$^{pos}$, CDK6$^{pos}$, E2F$^{pos}$, phospho-p107$^{pos}$, phospho-p130$^{pos}$, CCNA$^{pos}$, CCND1$^{pos}$, CCND2$^{pos}$, CCND3$^{pos}$, CCNE$^{pos}$, CDKN1a$^{neg}$, CDKN1b$^{neg}$, CDKN1c$^{neg}$, CDKN2a$^{neg}$, CDKN2b$^{neg}$, CDKN2c$^{neg}$, CDKN3$^{neg}$, c-kit$^{pos}$, CD3$^{neg}$, CD14$^{neg}$, CD68$^{neg}$, Nkx2.5$^{pos}$, MITF$^{pos}$, MEF2c$^{pos}$, and any combination thereof; and isolating the identified regenerative cardiomyocytes.

DESCRIPTION OF DRAWINGS

FIG. 1 shows the interactions between hMSCs/hCSCs induce endogenous regenerative activity via pRb$^{Ser608}$ in host cardiomyocytes and cardiac progenitors. (FIGS. 1A, 1B), Confocal immunofluorescence analysis reveals that expression of pRb$^{Ser608}$ (red nuclei) occurs in cardiomyocytes (yellow arrowheads) and Gata4$^+$ progenitors (arrows). A pRb$^{Ser608}$ cardiomyocyte exhibiting cytokinesis (yellow arrowhead with asterisk) and a very small, possibly newly formed, pRb$^{Ser608+}$ cardiomyocyte are delineated in (FIG. 1A). Cells not committed to cardiac lineage (white arrowheads) do not express pRb$^{Ser608}$. Tropomyosin (green, FIG. 1A) and Gata4 (white, FIG. 1B) were employed as markers to identify cardiomyocytes and/or cardiac progenitors, respectively. FIGS. 1C, 1D: The hCSCs-treated hearts have significantly higher concentrations of pRb$^{Ser608+}$/Gata4$^+$ progenitors compared to therapy with hMSCs or placebo, both in the infarct (FIG. 1C) and border zones (FIG. 1D). However, combination of hCSCs with hMSCs further enhanced this effect. FIGS. 1E, 1F: In addition to the expansion of the pRb$^{Ser608+}$ progenitor cell pool, animals treated with combination of cells, exhibited a significantly higher fraction of pRb$^{Ser608+}$ adult cardiomyocytes, both in the infarct (FIG. 1E) and border (FIG. 1F) zones compared to the other groups. N=3 animals/group; values are shown as means±SEM; *p≤0.0001. CPCs, Gata4$^+$ progenitors; CM, cardiomyocytes; hpf, high-power field.

FIG. 2 shows that the induction of pRb$^{Ser608+}$ in host CPCs does not relate to cell-cycling activity. FIGS. 2A, 2B: Confocal immunofluorescence against the mitotic marker HP3$^+$ demonstrates substantial numbers of Gata4$^+$ progenitors in mitosis in the infarct (FIG. 2A) and border zones of the porcine hearts. FIGS. 2C, 2D: Although stem cell treated hearts are invested with significantly higher numbers of pRb$^{Ser608+}$/Gata4$^+$ progenitors, the numbers of HP3$^+$/Gata4$^+$ progenitors in mitosis are not significantly different between groups, neither in the infarct (FIG. 2C), nor in border zones. Thus, induction of pRb$^{Ser608}$ following hCSCs/hMSCs interactions, is more likely to regulate cell-fate rather than cell-cycle decisions in Gata4$^+$ heart progenitors.

FIG. 3 shows that pRb$^{Ser608}$ and ARF repression in host cardiomyocytes by hMSC/hCSCs link to full cell cycle re-entry.

FIG. 4 shows that pRb$^{Ser608}$-regulated cardiomyocyte replication and progenitor cell commitment links to myocardial scar size reduction. Linear regression analyses of the cMRI-calculated percentage changes in scar size with.

FIG. 5 is a schematic representation of a summary of the study.

Figures 3A, 3B, 3C:
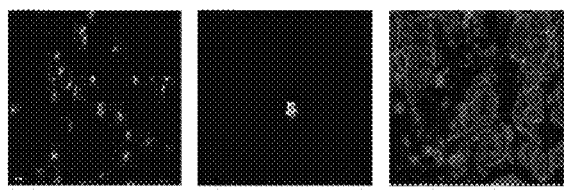
FIGS. 3A-3E: a mitotically dividing adult porcine cardiomyocyte in the infarct zone of human stem cell-treated hearts, as illustrated by expression of HP3. Laminin (red, FIG. 3C) highlights the cardiomyocyte borders with the extracellular matrix. In the merged image (FIG. 3D), the borders of healthy myocardium with the dead, scarred tissue are demarcated with a white line. Higher magnification of the mitotic cardiomyocyte (FIG. 3D, arrowhead) in FIG. 3E, illustrates cytokinesis, by the laminin+ borders (white lines).
Figures 3D, 3E:
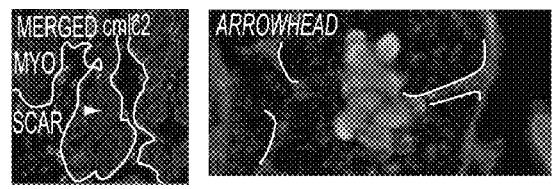
Figure 3H:
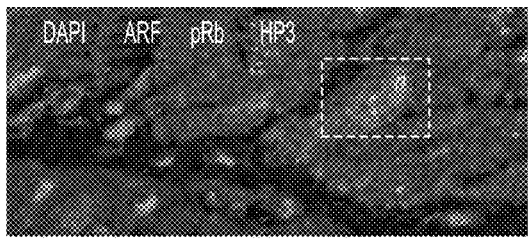
FIGS. 3H, 3I: A mitotically dividing cardiomyocyte (inset) in a hMSC/hCSC treated heart expressing HP3 (white, FIG. 3H) and pRb$^{Ser608}$ (red, FIG. 3I). Importantly, the dividing cell lacks expression of ARF (green nuclei), indicating the potential for undergoing additional rounds in cell cycle. This phenotype is consistent with the existence of an adult, transiently amplifying, regenerative cardiomyocytic population, with broader proliferative potentials than regular cardiomyocytes. White arrowheads depict pRb$^{Ser608}$-negative cardiomyocytes expressing ARF in their nucleus.
Figure 3I:
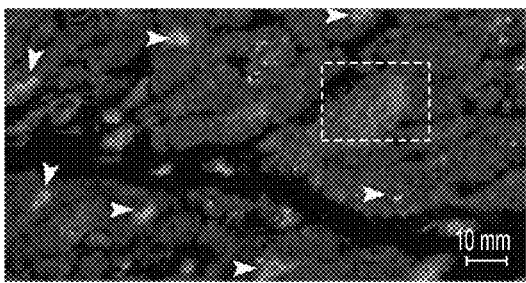
Figure 3F:
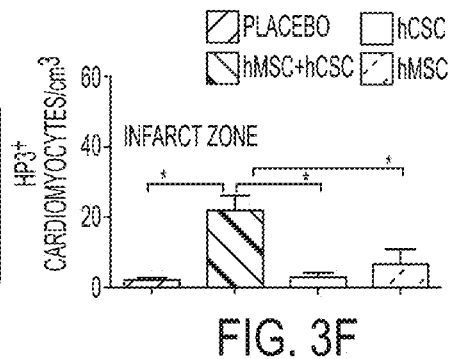
FIGS. 3F, 3G: the pools of mitotic cardiomyocytes in the infarct (FIG. 3F) and border (FIG. 3G) zones are dramatically expanded following hMSC/hCSC transplantation compared to the other groups.
Figure 3G:
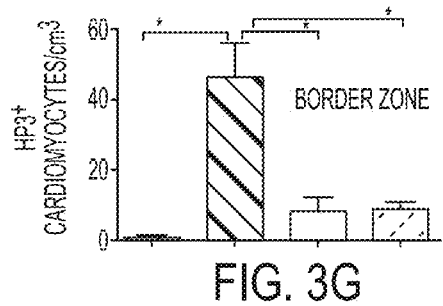
Figure 3J:
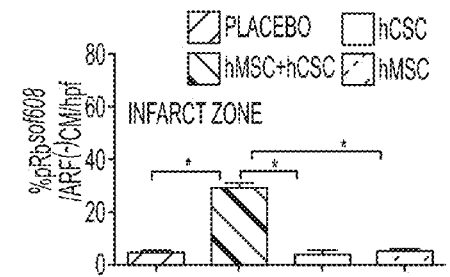
FIG. 3J, 3K: Compared to other groups, animals treated with the combination of hCSCs and hMSCs exhibit significantly higher rates in pRb$^{Ser608+}$/ ARF$^{(-)}$ cardiomyocytes, evidencing a novel mechanism of adult cardiomyocyte replication. CM, cardiomyocyte; hpf, high-power field.
Figure 3K:
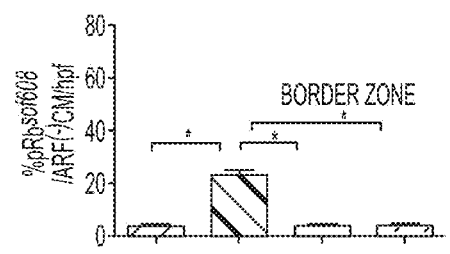
Figure 4A:
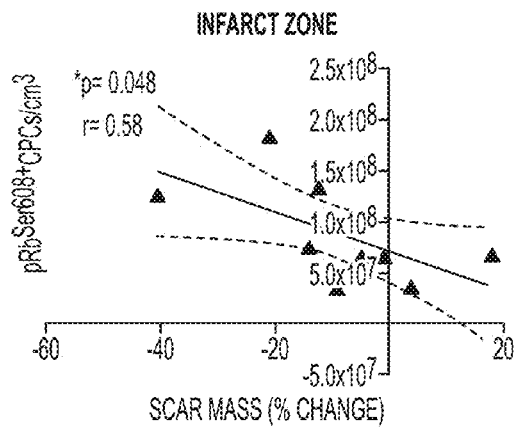
FIGS. 4A, 4B: the number of pRb$^{Ser608+}$/Gata4$^+$ progenitors in the infarct and border zones; the number of pRb$^{Ser608+}$ progenitors within the infarct (FIG. 4A), but not the border (FIG. 4B), zone correlates significantly with the reduction in scar size.
Figure 4B:
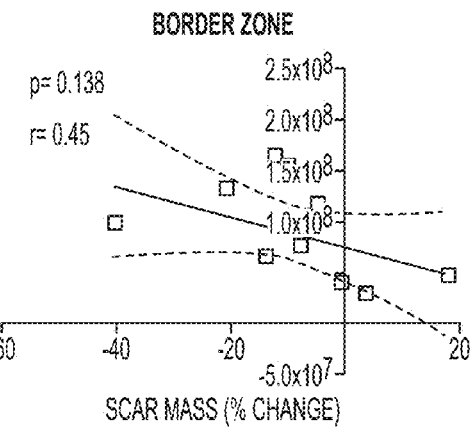
Figure 4C:
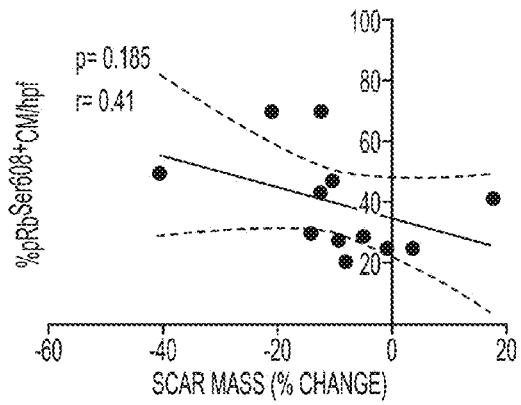
FIGS. 4C, 4D: the % of pRb$^{Ser608+}$ cardiomyocytes in the infarct and border zones; no correlation between scar size reduction and the % of pRb$^{Ser608+}$ cardiomyocytes was observed, in infarct (FIG. 4C) or border (FIG. 4D) zone. However, the % of pRb$^{Ser608+}$/ARF$^{(-)}$ cardiomyocytes in the infarct (FIG. 4E) and border (FIG. 4F) zones correlated significantly with the extent of myocardial scar shrinkage. Thus, pRb$^{Ser608+}$ followed by ARF repression is essential for full regenerative activity in cardiomyocytes.
Figure 4D:
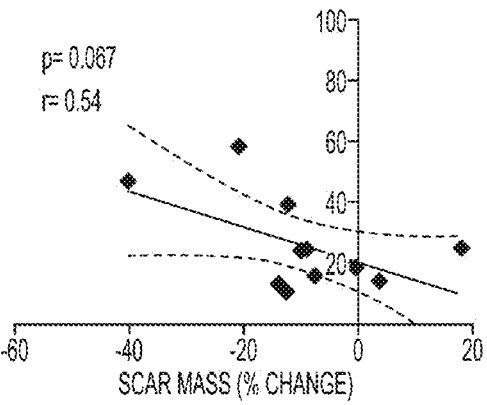
Figure 4E:
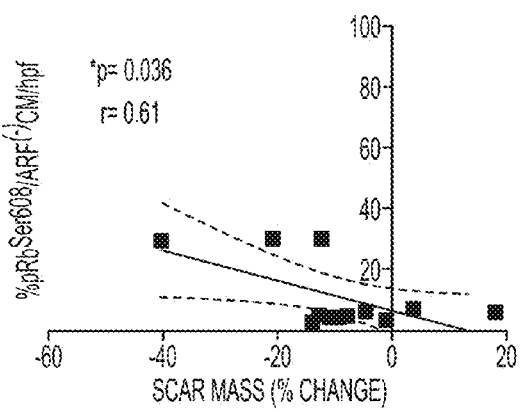
Figure 4F:
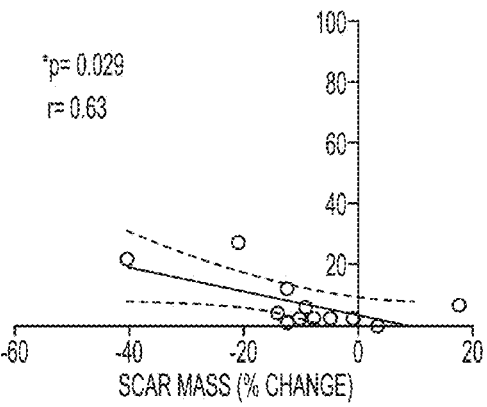
Figures 5A, 5B, 5C:
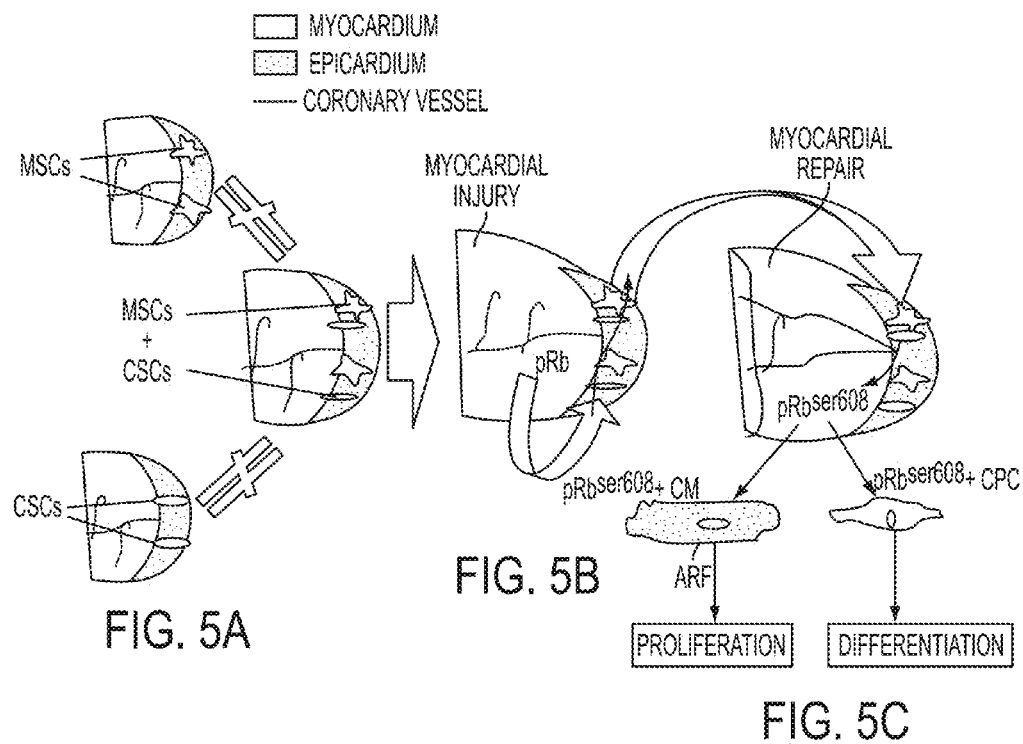
FIG. 5A shows that therapeutic transplantation of a combination of human mesenchymal and cardiac stem cells results in durable engraftment of human stem cells in ischemic porcine epicardium and perivascular sites.
FIG. 5B shows that the xenografted stem cell mixture, in contrast to each cell type alone, induces endogenous regenerative activity via pRb phosphorylation at ser-608.
FIG. 5C shows that this post-translational modification is propagated exclusively in cardiac lineage-specific cells and exhibits a dual effect. In conjunction with ARF repression, it restores full cell-cycling activity in host cardiomyocytes, whereas at the same time, activates regenerative Gata4$^+$ host progenitors. As a result, significant restoration of dead cardiac muscle occurs.
Figures 6A, 6B, 6C:
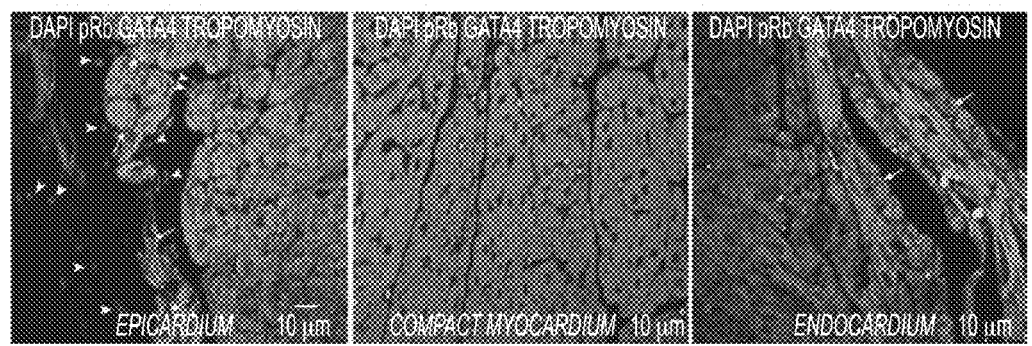
FIG. 6 shows the expression patterns of pRb$^{Ser608}$ in the healthy porcine heart. Confocal immunofluorescence analyses reveals that epicardial (FIG. 6A) and endocardial (FIG.
Figure 9E:
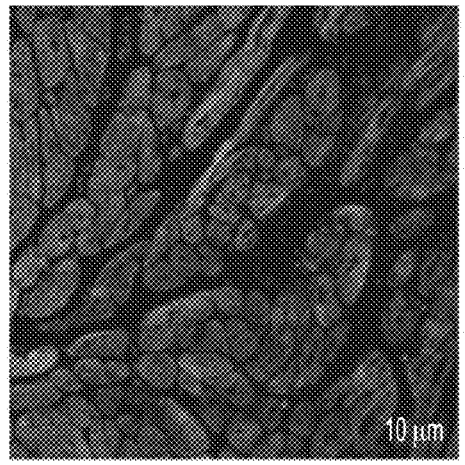
Figure 9F:
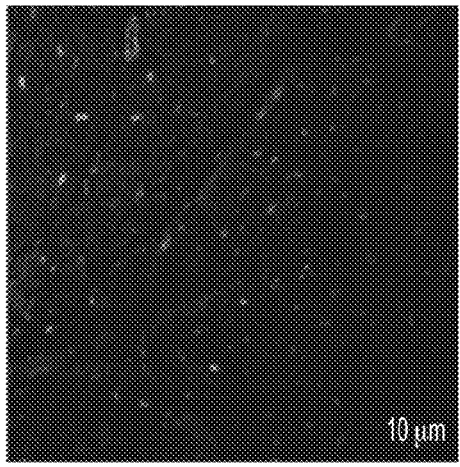
Figure 9G:
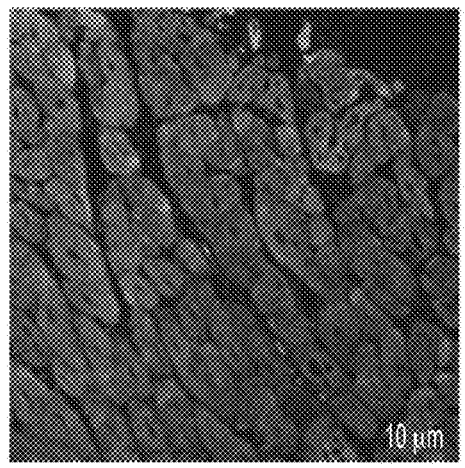
Figure 9H:
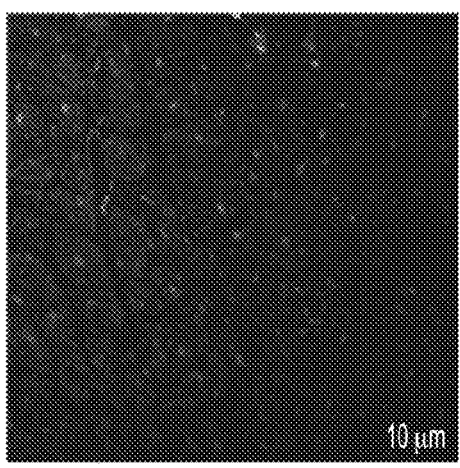

6C) cells, but not cells of the compact myocardial wall (FIG. 6B), exhibit pRb$^{Ser608}$ in the healthy porcine heart. Arrowheads indicate Gata4$^+$/pRb$^{Ser608+}$ progenitors; arrows indicate pRb$^{Ser608+}$ cardiomyocytes.

FIG. 7 shows that regenerative cardiomyocytes are significantly smaller than regular cardiomyocytes. FIG. 7A: Morphometric analyses of the cross-sectional area of HP3$^+$, mitotically dividing, cardiomyocytes in the hearts of human stem cell treated animals (blue bar) and non-mitotic cardiomyocytes in the placebo-treated group (black bar), reveals that the former are significantly smaller in size. FIGS. 7B, 7C: representative photomicrographs of an HP3$^+$ cardiomyocyte (FIG. 7B, inset) and non-dividing cardiomyocytes (FIG. 7C). Cardiac myosin light chain (cMLC2v, red) and Gata4 were used as cardiomyocyte markers.

FIG. 8 shows that pRb$^{Ser608+}$/ARF$^{(-)}$ cardiomyocytes correlate with mitotic activity. Linear regression analyses of the numbers of HP3+, mitotically dividing cardiomyocytes with the % of pRb$^{Ser608+}$ cardiomyocytes (FIG. 8A, and pRb$^{Ser608+}$/ARF$^{(-)}$ cardiomyocytes (FIG. 8B), reveals that the levels of pRb$^{Ser608}$ accurately predict the rates of cardiomyocyte mitosis. Regression is more robust when pRb$^{Ser608}$ is accompanied by an ARF-negative phenotype (FIG. 8B).

FIG. 9 shows that the induction of pRb$^{Ser608+}$/ARF$^{(-)}$ regenerative phenotype in cardiomyocytes requires both MSCs and CSCs. Representative confocal photomicrographs of porcine hearts treated with placebo (FIGS. 9A, 9B), hMSCs+hCSCs (FIGS. 9C, 9D), hCSCs. (FIGS. 9E, 9F) or hMSCs (FIGS. 9G, 9H), and immunostained for pRb$^{Ser608+}$ (red nuclei), ARF (white nuclei) and Tropomyosin (green). Notice the dramatic difference in pRb$^{Ser608+}$ cardiomyocytes following hMSCs+hCSCs treatment (FIGS. 9C, 9D), compared to the other groups. In addition, the vast majority of cardiomyocyte nuclei express the tumor suppressor ARF, resulting in cell cycle arrest. However, following transplantation of both hMSCs and hCSCs (FIGS. 9C, 9D), ARF expression becomes repressed in a significant fraction of host cardiac myocytes (inset and arrows in FIG. 9B).

Figure 10:
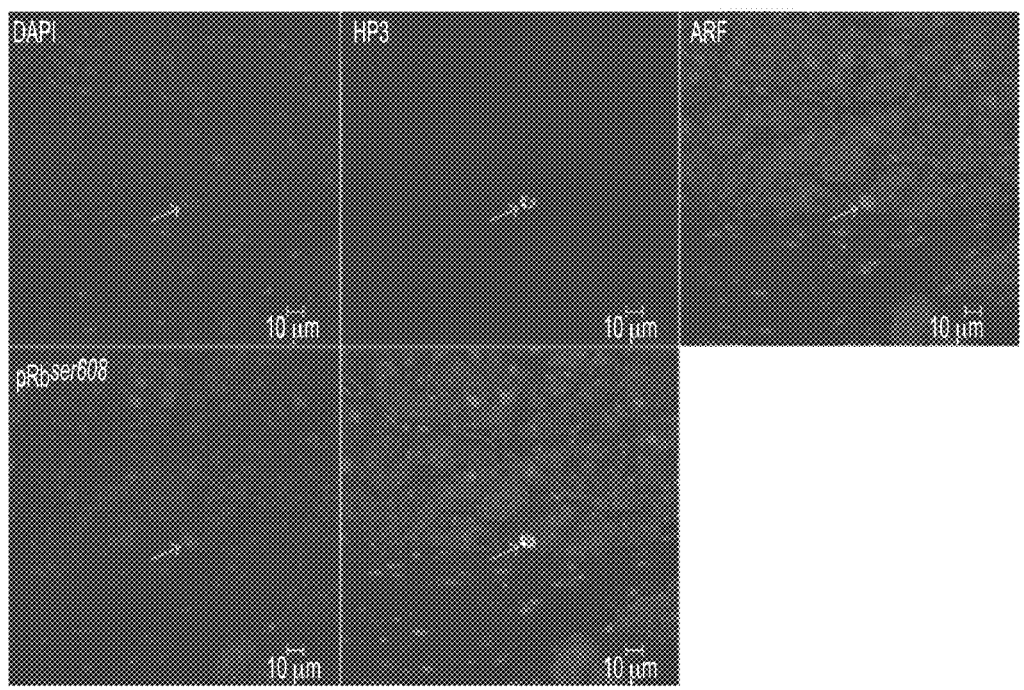

FIG. 10 shows that the majority of mitotically dividing cardiomyocytes express ARF. Confocal immunofluorescence depicts an HP3$^+$ (white), mitotically dividing cardiomyocyte (arrow), that co-expresses ARF (green) and pRb$^{ser608}$ (red). Expression of ARF restricts cardiomyocytes from undergoing additional cell cycles.

Figure 11:
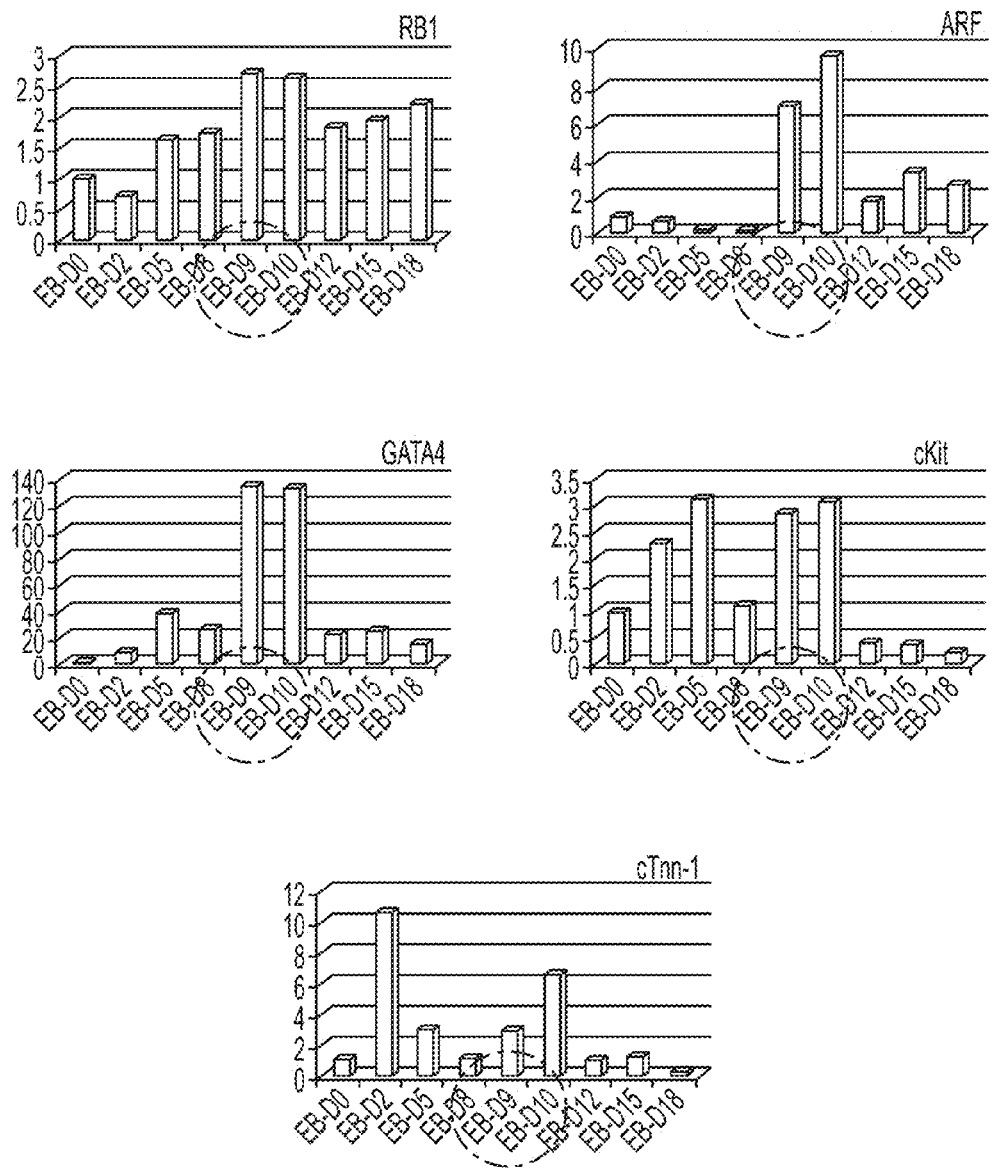

FIG. 11 shows relative gene expression analysis in human induced-pluripotentstem cells (hiPSCs) during cardiomyocyte differentiation. Values are normalized to embryoid bodies (EB) on day 0.

Figure 12A:
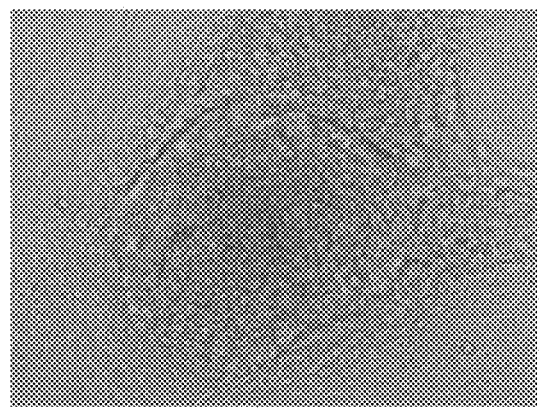
Figure 12B:
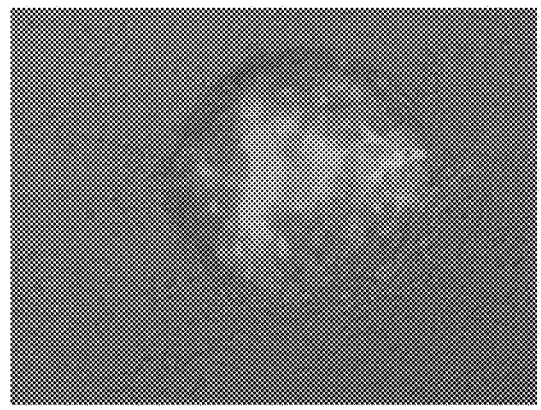

FIG. 12 demonstrates the knock-down of Rb in human embryonic stem cells (hESCs). FIGS. 12A and B show expression of GFP in hESCs in dox-untreated and dox-treated cells, respectively, as measured by fluorescent microscopy.

Figures 13A, 13B:
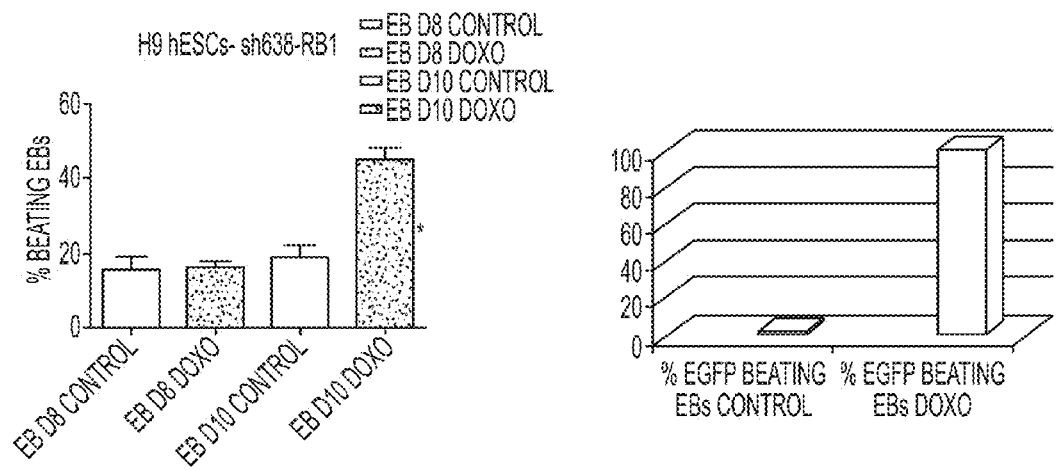
Figure 13C:
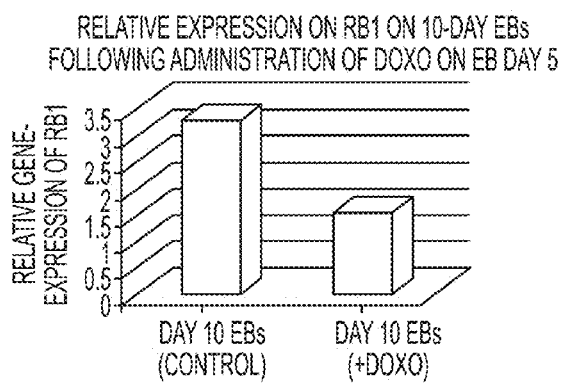

FIG. 13 demonstrate the knock-down of Rb in embryoid bodies. FIG. 13 A shows the quantification of beating embryoid bodies (EB) on day 8 and day 10. FIG. 13 B shows the fluorescent microscopy of GFP$^+$ cells in embryoid bodies at day 10. FIG. 13 C shows the expression of Rb in embryoid bodies on day 10.

Figure 14:
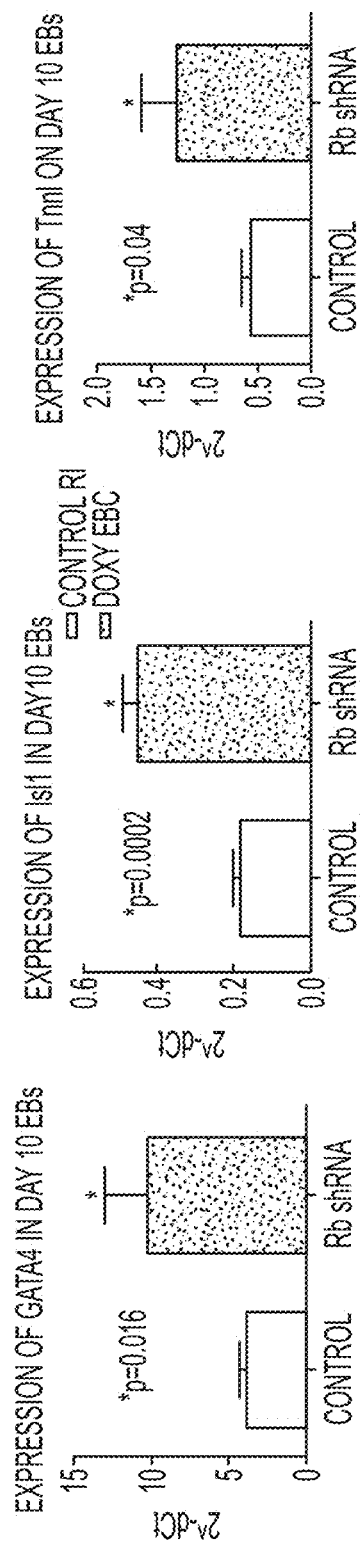

FIG. 14 shows gene expression analysis of Gata4, Isl1, and TnnI in day 10 EBs expressing control and Rb shRNA, according to an embodiment.

Figure 15:
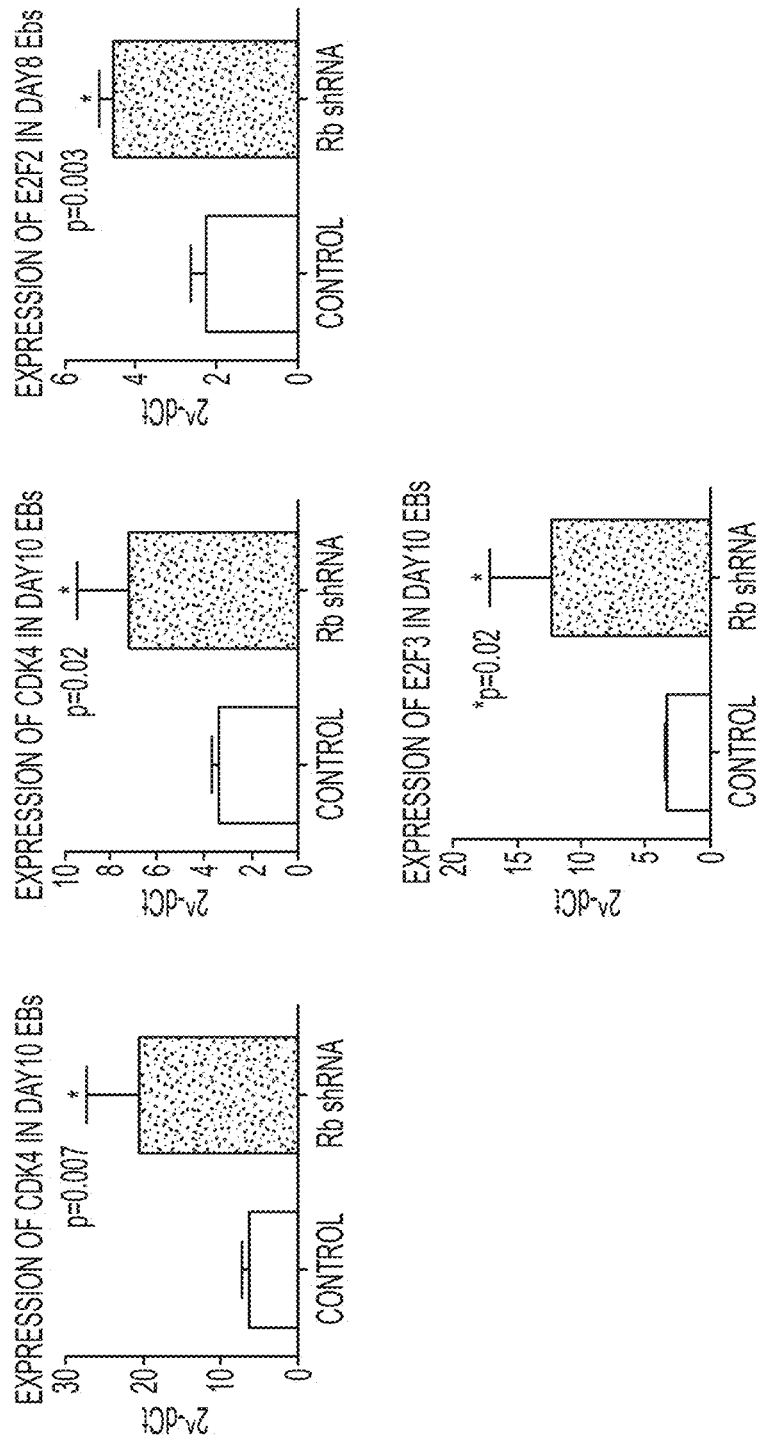

FIG. 15 demonstrates gene expression analysis of cell cycle activators in day 8-10 EBs expressing control and Rb shRNA, according to an embodiment.

Figure 16:
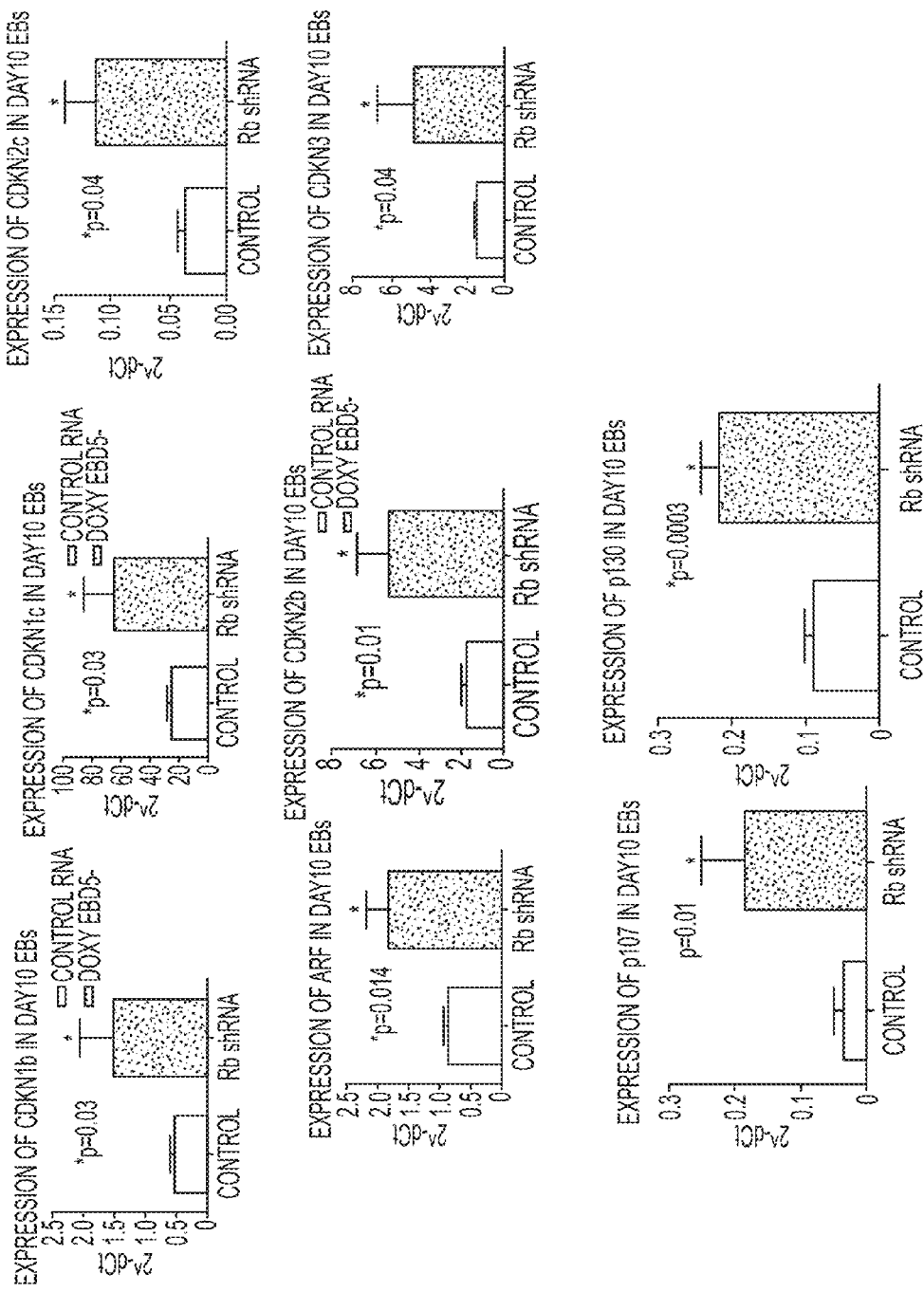

FIG. 16 shows gene expression analysis of cell cycle inhibitors in day 10 EBs expressing control and Rb shRNA, according to an embodiment.

DETAILED DESCRIPTION

Embodiments may be practiced without the theoretical aspects presented. Moreover, the theoretical aspects are presented with the understanding that the embodiments are not bound by any theory presented.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the proteins or genes disclosed herein, which in some embodiments relate to mammalian nucleic acid and amino acid sequences are intended to encompass homologous and/or orthologous genes and gene products from other animals including, but not limited to other mammals, fish, amphibians, reptiles, and birds. In some embodiments, the genes or nucleic acid sequences are human.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The terminology used herein is for the purpose of describing particular embodiments only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of ±10% of the referenced value.

"Administering" when used in conjunction with a therapeutic, means to administer a therapeutic directly into or onto a target tissue or to administer a therapeutic to a patient whereby the therapeutic positively impacts the tissue to which it is targeted. "Administering" a composition may be accomplished by oral administration, injection, infusion, parenteral, intravenous, mucosal, sublingual, intramuscular, subcutaneous absorption or by any method in combination with other known techniques. The therapeutic can also be implanted or placed at the site of treatment.

The term "animal," "patient," or "subject" as used herein includes, but is not limited to, humans and non-human vertebrates such as wild, domestic and farm animals. In some embodiments, the term refers to humans.

As used herein, the term "autologous" is meant to refer to any material derived from the same individual to whom it is later to be re-introduced into the individual.

The term "allogeneic cell" refers to a cell that is of the same animal species but genetically different in one or more genetic loci as the animal that becomes the "recipient host." This usually applies to cells transplanted from one animal to another non-identical animal of the same species. However, in some embodiments, cells from one species may be administered to a different species.

"Biological samples" include solid and body fluid samples. The biological samples used herein can include cells, protein or membrane extracts of cells, blood or biological fluids such as ascites fluid or brain fluid (e.g., cerebrospinal fluid). Examples of solid biological samples include, but are not limited to, samples taken from tissues of the central nervous system, bone, breast, kidney, cervix, endometrium, head/neck, gallbladder, parotid gland, prostate, pituitary gland, muscle, esophagus, stomach, small intestine, colon, liver, spleen, pancreas, thyroid, heart, lung, bladder, adipose, lymph node, uterus, ovary, adrenal gland, testes, tonsils and thymus. Examples of "body fluid samples" include, but are not limited to blood, serum, semen, prostate fluid, seminal fluid, urine, saliva, sputum, mucus, bone marrow, lymph, and tears. A biological sample can also include cardiac cells, cardiac progenitor cells, cardiac regenerative cells, or mature cardiomyocytes.

"Bone marrow derived progenitor cell" (BMDC) or "bone marrow derived stem cell" refers to a primitive stem cell with the machinery for self-renewal constitutively active. Included in this definition are stem cells that are totipotent, pluripotent and precursors. A "precursor cell" can be any cell in a cell differentiation pathway that is capable of differentiating into a more mature cell. As such, the term "precursor cell population" refers to a group of cells capable of developing into a more mature cell. A precursor cell population can comprise cells that are totipotent, cells that are pluripotent and cells that are stem cell lineage restricted (i.e. cells capable of developing into less than all hematopoietic lineages, or into, for example, only cells of erythroid lineage).

"Diagnostic" or "diagnosed" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

As used herein, "heart disease" refers to any type of heart disease including cardiovascular disease, myocardial stunning, peripheral vascular disease, cardiomyopathy, hypertrophic cardiomyopathy, dilated cardiomyopathy, atherosclerosis, coronary artery disease, ischemic heart disease, myocarditis, viral infection, wounds, hypertensive heart disease, valvular disease, congenital heart disease, myocardial infarction, congestive heart failure, arrhythmias, diseases resulting in remodeling of the heart, etc. Diseases of the heart can be due to any reason, such as for example, damage to cardiac tissue such as a loss of contractility (e.g., as might be demonstrated by a decreased ejection fraction). Heart disease may also result from intermittent claudication, tachycardia, ischemia-reperfusion, acute renal failure, stroke, hypotension, embolism, thromboembolism (blood clot), sickle cell disease, localized pressure to extremities to the body, tumors, and the like.

"Ischemia" refers to a lack of oxygen flow to the heart which results in myocardial ischemic damage. As used herein, the phrase myocardial ischemic damage includes damage caused by reduced blood flow to the myocardium. Non-limiting examples of causes of myocardial ischemia and myocardial ischemic damage include: decreased aortic diastolic pressure, increased intraventricular pressure and myocardial contraction, coronary artery stenosis (e.g., coronary ligation, fixed coronary stenosis, acute plaque change (e.g., rupture, hemorrhage), coronary artery thrombosis, vasoconstriction), aortic valve stenosis and regurgitation, and increased right atrial pressure. Ischemia may also be caused by heart surgery, organ transplantation, angioplasty, stenting, or any combination thereof. Non-limiting examples of adverse effects of myocardial ischemia and myocardial ischemic damage include: myocyte damage (e.g., myocyte cell loss, myocyte hypertrophy, myocyte cellular hyperplasia), angina (e.g., stable angina, variant angina, unstable angina, sudden cardiac death), myocardial infarction, and congestive heart failure. Damage due to myocardial ischemia may be acute or chronic, and consequences may include scar formation, cardiac remodeling, cardiac hypertrophy, wall thinning, dilatation, and associated functional changes. ischemia may also be caused due to heart diseases described herein. The existence and etiology of acute or chronic myocardial damage and/or myocardial ischemia may be diagnosed using any of a variety of methods and techniques well known in the art including, e.g., non-invasive imaging (e.g., MRI, echocardiography), angiography, stress testing, assays for cardiac-specific proteins such as cardiac troponin, and clinical symptoms. These methods and techniques as well as other appropriate techniques may be used to determine which subjects are suitable candidates for the treatment methods described herein.

By the term "modulate," it is meant that any of the mentioned activities described herein, are, e.g., increased, enhanced, increased, agonized (acts as an agonist), or promoted. Modulation can increase activity more than 1-fold, 2-fold, 3-fold, 5-fold, 10-fold, 100-fold, etc., over baseline values. Modulation can also decrease its activity below baseline values. Modulation can also normalize an activity to a baseline value.

The terms "patient" or "individual" are used interchangeably herein, and refers to a mammalian subject to be treated. In some embodiments, the patient is a human. In some cases, the methods can be used in experimental animals, in veterinary application, and in the development of animal models for disease, including, but not limited to, rodents including mice, rats, and hamsters; and primates. In some embodiments, the patient is a patient in need thereof.

As used herein, the phrase "in need thereof" means that the patient has been identified as having a need for the particular method or treatment. In some embodiments, the identification can be by any means of diagnosis. In any of the methods and treatments described herein, the animal or mammal can be in need thereof. In some embodiments, the animal or mammal is in an environment or will be traveling to an environment in which a particular disease, disorder, or condition is prevalent.

The term "syngeneic cell" refers to a cell which is of the same animal species and has the same genetic composition for most genotypic and phenotypic markers as the animal who becomes the recipient host of that cell line in a transplantation or vaccination procedure. This usually applies to cells transplanted from identical twins or may be applied to cells transplanted between highly inbred animals.

"Stem cell niche" refers to the microenvironment in which stem cells are found, which interacts with stem cells to regulate stem cell fate. (See, for example, Kendall Powell, Nature 435, 268-270 (2005). The word 'niche' can be in reference to the in vivo or in vitro stem cell microenvironment. During embryonic development, various niche factors act on embryonic stem cells to alter gene expression, and induce their proliferation or differentiation for the development of the fetus. Within the human body, stem cell niches maintain adult stem cells in a quiescent state, but after tissue injury, the surrounding microenvironment actively signals to stem cells to either promote self renewal or differentiation to form new tissues. Several factors are important to regulate stem cell characteristics within the niche: cell-cell interactions between stem cells, as well as interactions between stem cells and neighboring differentiated cells, interactions between stem cells and adhesion molecules, extracellular matrix components, the oxygen tension, growth factors, cytokines, and physiochemical nature of the environment including the pH, ionic strength (e.g. Ca2+ concentration, metabolites like ATP are also important. The stem cells and niche may induce each other during development and reciprocally signal to maintain each other during adulthood. The niche also refers to specific anatomic locations that regulate how they participate in tissue generation, maintenance and repair. The niche saves stem cells from depletion, while protecting the host from over-exuberant stem-cell proliferation. It constitutes a basic unit of tissue physiology, integrating signals that mediate the balanced response of stem cells to the needs of organisms. Yet the niche may also induce pathologies by imposing aberrant function on stem cells or other targets. The interplay between stem cells and their niche creates the dynamic system necessary for sustaining tissues, and for the ultimate design of stem-cell therapies.

"Treatment" is an intervention performed with the intention of preventing the development or altering the pathology or symptoms of a disorder. Accordingly, "treatment" can refer to therapeutic treatment or prophylactic or preventative measures. In some embodiments, the treatment is for therapeutic treatment. In some embodiments, the treatment is for prophylactic or preventative treatment. Those in need of treatment can include those already with the disorder as well as those in which the disorder is to be prevented. As used herein, "ameliorated" or "treatment" refers to a symptom which is approaches a normalized value (for example a value obtained in a healthy patient or individual), e.g., is less than 50% different from a normalized value, is less than about 25% different from a normalized value, is less than 10% different from a normalized value, or is not significantly different from a normalized value as determined using routine statistical tests.

Generally speaking, the term "tissue" refers to any aggregation of similarly specialized cells which are united in the performance of a particular function.

As used herein, the term "therapeutic" means an agent utilized to discourage, combat, ameliorate, prevent or improve an unwanted condition, disease or symptom of a patient.

A "therapeutically effective amount" or "effective amount" of an agent or a cell is a predetermined amount calculated to achieve the desired effect, i.e., to ameliorate, prevent or improve an unwanted condition, disease or symptom of a patient. The activity contemplated by the present methods includes both therapeutic and/or prophylactic treatment, as appropriate. The specific dose of the cells/agents administered according to the methods described herein to obtain therapeutic and/or prophylactic effects will, of course, be determined by the particular circumstances surrounding the case, including, for example, the cells/agents administered, the route of administration, and the condition being treated. The effective amount administered may be determined by a physician in the light of the relevant circumstances including the condition to be treated, the choice of cells/agents to be administered, and the chosen route of administration. A therapeutically effective amount of the cell/agent is typically an amount such that when it is administered in a physiologically tolerable excipient composition, it is sufficient to achieve an effective systemic concentration or local concentration in the target tissue. The cells can also be administered without excipients.

As used herein, the term "stem cell" refers to a cell from the embryo, fetus, or adult that has, under certain conditions, the ability to reproduce itself for long periods or, in the case of adult stem cells, throughout the life of the organism. It also can give rise to specialized cells that make up the tissues and organs of the body.

As used herein, the term, "pluripotent stem cell" refers to a cell that has the ability to give rise to types of cells that develop from the three germ layers (mesoderm, endoderm, and ectoderm) from which all the cells of the body arise. The only known sources of human pluripotent stem cells are those isolated and cultured from early human embryos and from fetal tissue that was destined to be part of the gonads.

As used herein the term, "embryonic stem cell" refers to a cell that is derived from a group of cells called the inner cell mass, which is part of the early (4- to 5-day) embryo called the blastocyst. Once removed from the blastocyst the cells of the inner cell mass can be cultured into embryonic stem cells. These embryonic stem cells are not themselves embryos.

Cells are referred to herein as being positive or negative for certain markers. For example, a cell can be positive for GATA, which can also be referred to as GATA$^{pos}$. The superscript notation "pos" refers to a cell that is positive for the marker linked to the superscript. In contrast a marker with the superscript "neg" refers to a cell that is negative for that marker. For example, a cell that is referenced as "ARF$^{neg}$" is negative for ARF. A "+" can also be used to reference that the marker as positive. A "−" can also be used to reference the marker as negative.

As used herein, the term "adult stem cell" refers to a cell that is an undifferentiated (unspecialized) cell that occurs in a differentiated (specialized) tissue, renews itself, and becomes specialized to yield all of the specialized cell types of the tissue in which it is placed when transferred to the appropriate tissue. Adult stem cells are capable of making identical copies of themselves for the lifetime of the organism. This property is referred to as "self-renewal." Adult stem cells usually divide to generate progenitor or precursor cells, which then differentiate or develop into "mature" cell types that have characteristic shapes and specialized functions, e.g., muscle cell contraction or nerve cell signaling. Sources of adult stem cells include bone marrow, blood, the cornea and the retina of the eye, brain, skeletal muscle, dental pulp, liver, skin, the lining of the gastrointestinal tract and pancreas.

As used herein, the term "totipotent cell" refers to a cell capable of developing into all lineages of cells. Similarly, the term "totipotent population of cells" refers to a composition of cells capable of developing into all lineages of cells. Also as used herein, the term "pluripotent cell" refers to a cell capable of developing into a variety (albeit not all) lineages and are at least able to develop into all hematopoietic lineages (e.g., lymphoid, erythroid, and thrombocytic lineages). Bone marrow derived stem cells contain two well-characterized types of stem cells. Mesenchymal stem cells (MSC) normally form chondrocytes and osteoblasts. Hematopoietic stem cells (HSC) are of mesodermal origin that normally give rise to cells of the blood and immune system (e.g., erythroid, granulocyte/macrophage, megakaryocyte and lymphoid lineages). In addition, hematopoietic stem cells also have been shown to have the potential to differentiate into the cells of the liver (including hepatocytes, bile duct cells), lung, kidney (e.g., renal tubular epithelial cells and renal parenchyma), gastrointestinal tract, skeletal muscle fibers, astrocytes of the CNS, Purkinje neurons, cardiac muscle (e.g., cardiomyocytes), endothelium and skin.

The term "xenogeneic cell" refers to a cell that derives from a different animal species than the animal species that becomes the recipient animal host in a transplantation or vaccination procedure.

Some embodiments disclosed herein are directed to markers predictive of cardiac regeneration in response to treatments, which can include the administration of cardiac cells. Prior to the embodiments described herein it was not known whether a patient's heart cells would regenerate after treatment because the mechanistic underpinnings of endogenous cellular replication in the adult mammalian heart were heretofore unknown.

Retinoblastoma protein (Rb), the tumor suppressor product of the retinoblastoma susceptibility gene, is a 110 kDa protein which plays an important role in regulating cell growth and differentiation. Central to the role of the Rb protein as a tumor suppressor is the ability of Rb to suppress inappropriate proliferation by arresting cells in the G1 phase of the cell cycle. Rb protein exerts its growth suppressive function by binding to transcription factors including E2F-1, PU.1, ATF-2, UBF, Elf-1, and c-Abl. The binding of Rb protein is governed by its phosphorylation state. Hypo- or under-phosphorylated forms of Rb bind and sequester transcription factors, most notably those of the E2F/DP family, inhibiting the transcription of genes required to traverse the G1 to S phase boundary of the cell cycle. This cell cycle inhibitory function is abrogated when Rb undergoes phosphorylation catalyzed by specific complexes of cyclins and cyclin-dependent protein kinases (cdks). In addition, Rb is also phosphorylated by non-cdks, such as MAP kinase, p38 kinase, JNK1, atypical protein kinase C, apoptotic signals, and the like. Thus, phosphorylation of Rb results in inhibition of its function.

The INK4a/ARF gene locus has been shown to encode two unrelated proteins from alternative but partially overlapping reading frames: (i) $p16^{Ink4a}$ and (ii) ARF ($p14^{ARF}$ in humans and $p19^{ARF}$ in the mouse). ARF stabilizes p53 by interfering with an auto-regulatory loop involving p53 and Double Minute 2 (Hdm2 in humans, Mdm2 in mice) that maintains p53 expression under normal cellular conditions. Mdm2 is known to bind p53 and inhibit the transactivation function of p53. Further, Mdm2 shuttles p53 from the nucleus to the cytoplasm and facilitates p53 degradation. In addition, Mdm2 also acts as an E3 ubiquitin ligase toward p53 within the ubiquitin-dependent 26S proteasome pathway. Therefore, Mdm2 inhibits p53 activity in the nucleus through multiple and diverse mechanisms. ARF, in-turn, inhibits Mdm2 activity and restores p53 levels and function. Loss of ARF results in decrease in p53 levels/function leading to cell cycle progression.

Stem cells from the bone marrow are the most-studied type of adult stem cells. They can be used clinically to restore various blood and immune components to the bone marrow via transplantation. There are currently identified two major types of stem cells found in bone marrow: hematopoietic stem cells (HSC, or $CD34^+$ cells) which are typically considered to form blood and immune cells, and stromal (mesenchymal) stem cells (MSC) that are typically considered to form bone, cartilage, muscle and fat. However, both types of marrow-derived stem cells recently have demonstrated extensive plasticity and multipotency in their ability to form the same tissues.

A "progenitor or precursor" cell occurs in fetal or adult tissues and is partially specialized; it divides and gives rise to differentiated cells. Researchers often distinguish precursor/progenitor cells from adult stem cells in that when a stem cell divides; one of the two new cells is often a stem cell capable of replicating itself again. In contrast when a progenitor/precursor cell divides, it can form more progenitor/precursor cells or it can form two specialized cells. Progenitor/precursor cells can replace cells that are damaged or dead, thus maintaining the integrity and functions of a tissue such as liver or brain.

Mesenchymal stem cells are the formative pluripotential blast cells found inter alia in bone marrow, blood, dermis and periosteum that are capable of differentiating into any of the specific types of mesenchymal or connective tissues (i.e. the tissues of the body that support the specialized elements; particularly adipose, osseous, cartilaginous, elastic, and fibrous connective tissues) depending upon various influences from bioactive factors, such as cytokines.

Certain methods of isolating and/or purifying mesenchymal stem cells have been described. In some embodiments, mesenchymal stem cells are isolated from bone marrow of adult patients. In some embodiments, the cells are passed through a density gradient to eliminate undesired cell types. The cells can be plated and cultured in appropriate media. In some embodiments, the cells are cultured for at least one day or about three to about seven days, and removing non-adherent cells. The adherent cells can then be plated and expanded.

Other methods for isolating and culturing stem cells useful are also known. Umbilical cord blood is an abundant source of hematopoietic stem cells. The stem cells obtained from umbilical cord blood and those obtained from bone marrow or peripheral blood appear to be very similar for transplantation use. Placenta is an excellent readily available source for mesenchymal stem cells. Moreover, mesenchymal stem cells can be derivable from adipose tissue and bone marrow stromal cells and speculated to be present in other tissues. While there are dramatic qualitative and quantitative differences in the organs from which adult stem cells can be derived, the initial differences between the cells may be relatively superficial and balanced by the similar range of plasticity they exhibit.

Homogeneous human mesenchymal stem cell compositions are provided which serve as the progenitors for all mesenchymal cell lineages. MSCs are identified by specific cell surface markers which are identified with unique monoclonal antibodies. The homogeneous MSC compositions are obtained by positive selection of adherent marrow or periosteal cells which are free of markers associated with either hematopoietic cell or differentiated mesenchymal cells. These isolated mesenchymal cell populations display epitopic characteristics associated with only mesenchymal stem cells, have the ability to regenerate in culture without differentiating, and have the ability to differentiate into specific mesenchymal lineages when either induced in vitro or placed in vivo at the site of damaged tissue.

In order to obtain subject human mesenchymal stem cells, pluripotent mesenchymal stem cells are separated from other cells in the bone marrow or other MSC source. Bone marrow cells may be obtained from iliac crest, femora, tibiae, spine, rib or other medullary spaces. Other sources of human mesenchymal stem cells include embryonic yolk sac, placenta, umbilical cord, fetal and adolescent skin, and blood.

In some embodiments, the mesenchymal stem cells are derived from one or sources comprising: autologous, heterologous, syngeneic, allogeneic or xenogeneic sources. These sources can include cell lines. As used herein, "source" refers to the animal in which these stem cells were obtained from, including human.

Differentiation of mesenchymal stem cells to the cardiac lineage is controlled by factors present in the cardiac environment. Local chemical, electrical and mechanical environmental influences alter pluripotent MSCs and convert the cells administered to the heart into the cardiac lineage.

In some embodiments, cardiac stem cells are identified by markers comprising: c-kit$^{pos}$, CD3$^{neg}$, CD14$^{neg}$ and CD68$^{neg}$. In some other embodiments, the cells are identified by the presence or absence of markers as described herein.

Disclosed herein are methods to identify and isolate cardiac progenitor cells. Without wishing to be bound by theory, phosphorylated Rb (pRb) activity governs the endogenous cell proliferative and fate commitment in the host response to cell therapy. The embodiments described herein show that the interactions between mesenchymal stem cells (MSCs) and cardiac stem cells (CSCs), rendered the host myocardium permissive for pRb and alternate reading frame of Ink4a (ARF) to regulate heart regeneration. Furthermore, identified were replicating myocytes, differentiating progenitors, and a pool of transient amplifying precursors as the endogenous regenerative cell sources. These mechanisms recapitulate key features of the adult mammalian stem cell niche and, therefore, support a role for stem cell niches in the mammalian heart's regenerative repertoire.

A novel cell type was generated and identified. Some embodiments are provided in the examples section which follows. In some embodiments, a novel cell comprises properties identified as a transiently amplifying, regenerative cardiomyocytic cell, with broader proliferative potentials than regular cardiomyocytes. Additionally, morphometric analysis illustrated that the cross-sectional areas of these newly formed cardiomyocytes were significantly smaller compared to cardiomyocytes in the placebo treated group ($p<0.05$), providing evidence that they are transient amplifying progeny of host CPCs (see, e.g., FIG. 7). The abundance of pRb$^{Ser608}$ correlated significantly with the numbers of cardiomyocytes in mitosis (FIG. 8A), further supporting the conclusion that hMSCs/hCSCs interactions induce pRb$^{Ser608}$ inactivation and the subsequent regulation of cardiomyocyte cell-cycle activity. In some embodiments, an isolated cell comprises markers: HP3$^+$, pRb$^{Ser608+}$ and Gata4$^+$. In some embodiments, the isolated cell is ARF-negative. In some embodiments, the cell is a mammalian cell.

In some embodiments, a method of isolating regenerative cardiomyocytes from a population of cardiomyocytes may comprise identifying the regenerative cardiomyocytes in the population as cells that are positive for at least one marker selected from phospho-Rb$^{pos}$, Gata4$^{pos}$, ARF$^{neg}$, N-cadherin$^{pos}$, connexin-43$^{pos}$, Isl1$^{pos}$, Wt1$^{pos}$, CDK2$^{pos}$, CDK4$^{pos}$, CDK6$^{pos}$, E2F$^{pos}$, phospho-p107$^{pos}$, phospho-p130$^{pos}$, CCNA$^{pos}$, CCND1$^{pos}$, CCND2$^{pos}$, CCND3$^{pos}$, CCND3$^{pos}$, CCNE$^{pos}$, CDKN1a$^{neg}$, CDKN1b$^{neg}$, CDKN1c$^{neg}$, CDKN2a$^{neg}$, CDKN2b$^{neg}$, CDKN2c$^{neg}$, CDKN3$^{neg}$, c-kit$^{pos}$, CD3$^{neg}$, CD14$^{neg}$, CD68$^{neg}$, Nkx2.5$^{pos}$, MITF$^{pos}$, MEF2c$^{pos}$, and any combination thereof; and isolating the identified regenerative cardiomyocytes. In some embodiments, the population of cardiomyocytes contains mature cardiomyocytes.

In some embodiments, the cardiomyocytes that are phospho-Rb$^{pos}$ are identified as regenerative cardiomyocytes. In some embodiments, the cardiomyocytes that are phospho-Rb$^{pos}$ and Gata4$^{pos}$ are identified as regenerative cardiomyocytes. In some embodiments, the cardiomyocytes that are phospho-Rb$^{pos}$ and ARF$^{neg}$ are identified as regenerative cardiomyocytes. In some embodiments, the cardiomyocytes that are phospho-Rb$^{pos}$, Gata4$^{pos}$, and ARF$^{neg}$ are identified as regenerative cardiomyocytes. In some embodiments in addition to the presence or markers referenced above, the cardiomyocytes that have at least one, at least two, at least three, at least four, or at least five additional markers selected from the group consisting of N-cadherin$^{pos}$, connexin-43$^{pos}$, Isl1$^{pos}$, Wt1$^{pos}$, CDK2$^{pos}$, CDK4$^{pos}$, CDK6$^{pos}$, E2F$^{pos}$, phospho-p107$^{pos}$, phospho-p130$^{pos}$, CCNA$^{pos}$, CCND1$^{pos}$, CCND2$^{pos}$, CCND3$^{pos}$, CCNE$^{pos}$, CDKN1a$^{neg}$, CDKN1b$^{neg}$, CDKN1c$^{neg}$, CDKN2a$^{neg}$, CDKN2b$^{neg}$, CDKN2c$^{neg}$, CDKN3$^{neg}$, c-kit$^{pos}$, CD3$^{neg}$, CD14$^{neg}$, CD68$^{neg}$, Nkx2.5$^{pos}$, MITF$^{pos}$, MEF2c$^{pos}$ are identified as regenerative cardiomyocytes. In some embodiments, the cardiomyocytes having all the markers are identified as regenerative cardiomyocytes.

In some embodiments, isolating the identified regenerative cardiomyocytes may be performed by any known technique in the art, such as, but not limited to, fluorescence assisted cell sorter (FACS), laser scanning cytometry, fluorescent microscopy, RT-PCR, DNA hybridization, fluorescence in situ hybridization, mass spectroscopy, microarray, immunohistochemistry, or any combination thereof. The methods of isolation are not critical and any method can be used so long as the isolation utilizes the presence or absence of markers described herein.

Also disclosed herein are methods to generate regenerating cells. In some embodiments, a method of generating a regenerative cell comprises co-culturing of mesenchymal stem cells (MSCs), cardiac stem cells (CSCs) or combinations of MSCs and CSCs in vitro, or administering to a subject in need of treatment: mesenchymal stem cells (MSCs), cardiac stem cells (CSCs) or combinations of MSCs and CSCs. In some embodiments, the regenerative cell comprises a phenotype identified by markers HP3$^+$/pRb$^{Ser608}$+/Gata4$^+$//ARF-negative. In some embodiments, the regenerative cell comprises a phenotype identified by markers pRb$^{Ser608+}$, Gata4$^+$, and ARF$^-$. In some embodiments, a progenitor cell may be formed by the process of co-culturing mesenchymal stem cells (MSCs) and cardiac stem cells (CSCs) in vitro or in vivo, wherein the progenitor cell comprises a phenotype identified by markers positive for phosphorylated retinoblastoma serine 608 (pRb$^{Ser608}$) and/or Gata4 (Gata4$^+$). The progenitor cell may be a cardiac progenitor cell (CPC). In some embodiments, the progenitor cell may be ARF negative.

Gata-4 can be used as a cardiomyocyte marker. GATA transcription factor includes members of the GATA family of zinc finger transcription factors. GATA transcription factors are involved in the development of several mesodermally derived cell lineages. GATA transcription factors include GATA-4 and/or GATA-6. The GATA-6 and GATA-4 proteins share high-level amino acid sequence identity over a proline-rich region at the amino terminus of the protein that is not conserved in other GATA family members.

Detection of expression of additional cardiomyocyte specific proteins can be achieved by using antibodies to, for example, myosin heavy chain monoclonal antibody MF 20 (MF20), sarcoplasmic reticulum calcium ATPase (SERCA1) (mnAb 10D1) or gap junctions using antibodies to connexin 43. Other markers for cardiomyocytes comprise cardiac troponin I (cTnI), cardiac troponin T (cTnT), sarcomeric myosin heavy chain (MHC), GATA-4, Nkx2.5, N-cadherin, β1-adrenoceptor β1-AR), ANF, the MEF-2 family of transcription factors, creatine kinase MB (CK-MB), myoglobin, or atrial natriuretic factor (ANF). Antibodies can also be used to detect any or all of the markers described herein.

Also disclosed herein are methods to isolate regenerating progenitor cells. In some embodiments, a method of isolating cardiac progenitor cells from a population of cardiac cells may comprise identifying the cardiac progenitor cells in the population as cells comprising phosphorylated retinoblastoma protein; and isolating the identified cardiac progenitor cells. In some embodiments, the cardiac progenitor cells are identified by contacting the population of cardiac cells with an agent that detects phosphorylated Rb. In some embodiments, the agent may detect hyperphosphorylated Rb. In some embodiments, the agent may detect any of the 16 putative phosphorylated serine or threonine residues, including Ser-249, Thr-252, Thr-373, Thr-356, Ser-608, Ser-780, Ser-795, Ser-807, Ser-811, Thr-821, and Thr-826. In some embodiments, Rb is phosphorylated at Ser-608. In some embodiments, the agent that detects phosphorylated Rb may be an antibody. Antibodies against phosphorylated Rb are known in the art and any such antibody may be used. For example, an antibody that binds to Rb at phosphorylated Ser 608 may be used.

In some embodiments, the isolated cardiac progenitor cells that are identified because of phosphorylated retinoblastoma protein are also positive for Gata4 (Gata4$^+$). In some embodiments, the isolated cardiac progenitor cells that are identified because of phosphorylated retinoblastoma protein are also are negative for ARF (ARF$^-$). In some embodiments, the isolated cardiac progenitor cells that are identified because of phosphorylated retinoblastoma protein are also positive for Gata4 (Gata4$^+$) and negative for ARF (ARF$^-$).

In some embodiments, the agent or the antibody described herein may further comprise a detectable label, such as a chromophore, a fluorophore, a chemiluminescent compound, an enzyme, a metal ion, and any combination thereof. In some embodiments, a secondary antibody that specifically recognizes the primary anti-pRb antibody may be used. The secondary antibody may be conjugated to detectable labels, such as peroxidases (example, horseradish or soybean peroxidase), alkaline phosphatase, β-galactosidase, chelated lanthanides, biotin, radiolabels, chromophores, fluorophores, and the like. The term "labeled", with regard to the probe or antibody, can also encompass direct-labeling of the probe or antibody by coupling, i.e., physically linking, a detectable substance to the probe or antibody, as well as indirect-labeling of the probe or antibody by reactivity with another reagent that is directly-labeled. Examples of indirect labeling include detection of a primary antibody using a fluorescently-labeled secondary antibody and end-labeling of a DNA probe with biotin such that it can be detected with fluorescently-labeled streptavidin.

Once the cardiac progenitor cells expressing phosphorylated Rb are identified, the identified cells may be sorted from the remaining population of cells. Non-limiting examples of sorting techniques that may be used are fluorescence assisted cell sorter (FACS), fluorescent plate reader, laser scanning cytometer, fluorescent microscope, or any combination thereof. The isolated cardiac progenitor cells may be positive for Gata4 (Gata4$^+$) and/or negative for ARF (ARF$^-$).

In some embodiments, the isolated cardiac progenitor cells described herein may be administered to a subject in need of such administration. For example, the subject may have a heart disease, a heart disorder, such as ischemia. Without wishing to be bound by theory, the administered cardiac progenitor cells may differentiate into mature cardiomyoctes at the site of injury, and help in healing cardiac tissue. Examples of heart disease include, but are not limited to cardiovascular disease, cardiomyopathy, myocardial stunning, peripheral vascular disease, intermittent claudication, tachycardia, ischemia-reperfusion, myocardial infarction, acute renal failure, stroke, hypotension, embolism, thromboembolism (blood clot), sickle cell disease, localized pressure to extremities to the body, tumors, and any combination thereof.

In some embodiments, a method of isolating cardiac progenitor cells from a population of cardiac cells may comprise identifying the cardiac progenitor cells in the population as cells that are positive for at least one marker selected from phospho-Rb$^{pos}$, Gata4$^{pos}$, ARF$^{neg}$, and any combination thereof; and isolating the identified cardiac progenitor cells. In some embodiments, the cells that are positive for phospho-Rb$^{pos}$ and Gata4 are identified as cardiac progenitor cells. In some embodiments, the cells that are positive for phospho-Rb$^{pos}$ and negative for ARF are identified as cardiac progenitor cells. In some embodiments, the cells that are positive for Gata4 and negative for ARF are identified as cardiac progenitor cells. In some embodiments, the cells that are positive for at phospho-Rb$^{pos}$ and Gata4, and negative for ARF are identified as cardiac progenitor cells. In some embodiments, the identified cardiac progenitor cells are N-cadherin$^{pos}$, connexin-43$^{pos}$, Isl1$^{pos}$, Wt1$^{pos}$, CDK2$^{pos}$, CDK4$^{pos}$, CDK6$^{pos}$, E2F$^{pos}$, phospho-p107$^{pos}$, phospho-p130$^{pos}$, CCNA$^{pos}$, CCND1$^{pos}$, CCND2$^{pos}$, CCND3$^{pos}$, CCNE$^{pos}$, c-kit$^{pos}$, CD3$^{neg}$, CD14$^{neg}$, CD68$^{neg}$, Nkx2.5$^{pos}$, MITF$^{pos}$, MEF2c$^{pos}$, or any combination thereof.

In some embodiments, the isolated cardiac progenitor cells may also have the following markers: N-cadherin$^{pos}$, connexin-43$^{pos}$, Isl1$^{pos}$, Wt1$^{pos}$, CDK2$^{pos}$, CDK4$^{pos}$, CDK6$^{pos}$, E2F$^{pos}$, phospho-p107$^{pos}$, phospho-p130$^{pos}$, CCNA$^{pos}$, CCND1$^{pos}$, CCND2$^{pos}$, CCND3$^{pos}$, CCNE$^{pos}$, c-kit$^{pos}$, CD3$^{neg}$, CD14$^{neg}$, CD68$^{neg}$, Nkx2.5$^{pos}$, MITF$^{pos}$, MEF2c$^{pos}$, or any combination thereof. The negative expression of the marker implies that the level of expression of the protein or the mRNA in the progenitor cells is relatively low or absent when compared to non-progenitor cells The markers described herein may identified by any techniques known in the art, such as but not limited to, fluorescence assisted cell sorter (FACS), laser scanning cytometry, fluorescent microscopy, RT-PCR, DNA hybridization, fluorescence in situ hybridization, mass spectroscopy, microarray, immunohistochemistry, and any combination thereof. The cells can also be isolated by any known method, including, but not limited to, cell sorting.

In some embodiments, the method further comprises identifying cells that are N-cadherin$^{pos}$, connexin-43$^{pos}$, Isl1$^{pos}$, Wt1$^{pos}$, CDK2$^{pos}$, CDK4$^{pos}$, CDK6$^{pos}$, E2$^{pos}$, phospho-p107$^{pos}$, phospho-p130$^{pos}$, CCNA$^{pos}$, CCND1$^{pos}$, CCND2$^{pos}$, CCND3$^{pos}$, CCNE$^{pos}$, c-kit$^{pos}$, CD3$^{neg}$, CD14$^{neg}$, CD68$^{neg}$, Nkx2.5$^{pos}$, MITF$^{pos}$, MEF2c$^{pos}$, or any combination thereof prior to isolating the identified cardiac progenitor cells.

In an additional embodiment, a composition may comprise an isolated population of cardiac progenitor cells obtained according to the methods described herein.

In some embodiments, a method of isolating cardiac progenitor cells from a population of cardiac cells may comprise introducing into the cardiac cells a nucleic acid sequence encoding for a reporter protein and an inhibitor of Rb; screening the cells expressing the reporter protein; and isolating the cells expressing the reporter protein, wherein isolated cells contain decreased levels of Rb protein when compared to cells not expressing the reporter protein. In some embodiments, the reporter protein and the inhibitor may be encoded by different DNA molecules. In some embodiments, the reporter protein and the inhibitor may be encoded by a single DNA molecule. The nucleic acid that is introduced into the cardiac cells may be a plasmid, a vector, or a DNA fragment. In some embodiments, the vector may be a plasmid, cosmid, virus, bacteriophage, or any another vector that is conventionally used in genetic engineering.

In some embodiments, the reporter protein may be green fluorescent protein (GFP), enhanced green fluorescent protein (EGFP), enhanced yellow fluorescent protein (EYFP), blue fluorescent protein (BFP), enhanced blue florescent protein (EBFP), or enhanced cyan fluorescent protein (ECFP). Additionally, the presence of reporter protein in the nuclei acid sequence has the advantage of tracking cells that express the inhibitor.

In some embodiments, the Rb inhibitor may be RNA interference (RNAi) molecules, such as small interfering RNA (siRNA), small hairpin RNA (shRNA), microRNA (miRNA), hybrid of miRNA, and shRNA, and antisense RNA. The structure and function of short hairpin RNA molecules are well-known to a skilled person. Short hairpin RNA is capable of mediating gene knockdown in a process termed RNA interference. Once a shRNA molecule is transcribed in the cell, it is cleaved by an RNase III-like enzyme (Dicer) into double stranded small interfering RNAs (siRNA), and loses its loop structure. In an ATP dependent step, the siRNAs become integrated into a multi-subunit protein complex, commonly known as the RNAi induced silencing complex (RISC), which guides the siRNAs to the target RNA sequence. At some point during the integration phase, the siRNA duplex unwinds, and the antisense strand remains bound to RISC and directs degradation of the complementary mRNA sequence by a combination of endo- and exo-nucleases.

The nuclei acid sequence may be introduced into the cardiac cells by any technique known in the art, such as transfection, viral transduction, electroporation, and the like. In some embodiments, the nuclei acid sequence may be part of a lentivirus construct, retrovirus construct, adenovirus construct, or any other plasmid constructs routinely used in the art. In some embodiments, conditional vectors may be used that allow for regulated expression of shRNA molecules and thus expression can be turned on leading to knockdown of the target gene in a tissue-specific and/or time dependent manner. Regulation can be achieved by using an inducing compound such as, for example, doxycycline or tetracycline which acts on artificial regulatory sequences in the polymerase III promoter.

Once the cardiac progenitor cells expressing the reporter protein are identified, the identified cells may be sorted from the population of cells. Non-limiting examples of sorting techniques that may be used are fluorescence assisted cell sorter (FACS), fluorescent plate reader, laser scanning cytometer, fluorescent microscope, or any combination thereof. The isolated cells may be further confirmed by assays to detect the expression levels of Rb protein. Such assays may be Western blotting, RT-PCR, ELISA, immunohistochemistry, and the like. Further, the isolated cardiac progenitor cells may also be positive for Gata4 (Gata4$^+$), and negative for ARF (ARF$^-$).

Disclosed herein are also methods to treat a subject having a heart disease. Heart disease (cardiac damage or disorder) characterized by insufficient cardiac function includes any impairment or absence of a normal cardiac function or presence of an abnormal cardiac function. Abnormal cardiac function can be the result of disease, injury, and/or aging. As used herein, abnormal cardiac function includes morphological and/or functional abnormality of a cardiomyocyte, a population of cardiomyocytes, or the heart itself. Non-limiting examples of morphological and functional abnormalities include physical deterioration and/or death of cardiomyocytes, abnormal growth patterns of cardiomyocytes, abnormalities in the physical connection between cardiomyocytes, under- or over-production of a substance or substances by cardiomyocytes, failure of cardiomyocytes to produce a substance or substances which they normally produce, and transmission of electrical impulses in abnormal patterns or at abnormal times. Abnormalities at a more gross level include dyskinesis, reduced ejection fraction, changes as observed by echocardiography (e.g., dilatation), changes in EKG, changes in exercise tolerance, reduced capillary perfusion, and changes as observed by angiography. Abnormal cardiac function is seen with many disorders including, for example, ischemic heart disease, e.g., angina pectoris, myocardial infarction, chronic ischemic heart disease, hypertensive heart disease, pulmonary heart disease (cor pulmonale), valvular heart disease, e.g., rheumatic fever, mitral valve prolapse, calcification of mitral annulus, carcinoid heart disease, infective endocarditis, congenital heart disease, myocardial disease, e.g., myocarditis, dilated cardiomyopathy, hypertensive cardiomyopathy, cardiac disorders which result in congestive heart failure, and tumors of the heart, e.g., primary sarcomas and secondary tumors. Heart damage also includes wounds, such as for example, knife wound; biological (e.g. viral; autoimmune diseases) or chemical (e.g. chemotherapy, drugs); surgery; transplantation and the like.

In some embodiments, a method of treating a heart disease in a subject in need thereof may comprise administering a therapeutically effective amount of cardiac progenitor cells that are disclosed herein. The subject may suffer from the heart disease due to a cardiovascular disease, cardiomyopathy, myocardial stunning, peripheral vascular disease, intermittent claudication, tachycardia, ischemia-reperfusion, myocardial infarction, acute renal failure, stroke, hypotension, embolism, thromboembolism (blood clot), sickle cell disease, localized pressure to extremities to the body, tumors, and combinations thereof. Heart disease may also be due to morphological and functional abnormalities of the heart, insufficient cardiac function, and heart damage as described herein. The administered cardiac progenitor cells may have a phenotype expressing markers, such as Gata4 (Gata4+), and negative for ARF (ARF−). In addition, the cardiac progenitor cells may lack Rb function due to phosphorylation of Rb or may lack Rb expression.

Disclosed herein are methods to treat a subject having ischemia. Tissues deprived of blood and oxygen undergo ischemic necrosis or infarction with possible irreversible organ damage. Once the flow of blood and oxygen is restored to the organ or tissue (reperfusion), the organ does not immediately return to the normal preischemic state. Reperfusion of the blood flow is necessary to resuscitate the ischemic or hypoxic tissue or organ. Timely reperfusion facilitates salvage of cells and decreases morbidity and mortality. However, reperfusion of an ischemic area may result in a paradoxical dysfunction including marked endothelial cell dysfunction, which results in vasoconstriction, and acute immune response due to platelet and leukocyte activation, increased oxidant production, and increased fluid and protein extravasation.

In some embodiments, a method of treating an ischemic disorder in a subject in need thereof may comprise administering a therapeutically effective amount of an agent that inhibits the function of retinoblastoma (Rb) and/or alternate reading frame of Ink4a (ARF) in cardiac cells. In some embodiments, the ischemic disorder may be caused by heart surgery, organ transplantation, angioplasty, stenting, or any combination thereof. In addition, the ischemic disorder may also be due to cardiovascular disease, cardiomyopathy, myocardial stunning, peripheral vascular disease, intermittent claudication, tachycardia, ischemia-reperfusion, myocardial infarction, acute renal failure, stroke, hypotension, embolism, thromboembolism (blood clot), sickle cell disease, localized pressure to extremities to the body, tumors, and any combination thereof.

The agents that may be used to treat ischemic disorder may be agents that inhibit Rb function and/or ARF function. Such inhibition would result in cell-cycle progression and proliferation of cardiomyocytes and/or cardiac progenitor cells, resulting in healing of the injured tissue. Non-limiting of agents that may be used are RNAi molecules that inhibit Rb and/or ARF expression, such as siRNA inhibitor, a shRNA inhibitor, or an antisense nucleotide inhibitor. In some embodiments, agents may also be a peptide mimetic inhibitor, a small molecule, an antibody, a kinase that phosphorylates Rb, a transcriptional repressor of ARF, or any combination thereof.

In some embodiments, the agent may also increase the phosphorylation of Rb in cardiac cells. For example, RNAi molecules that target cdk inhibitors (cip/kip family and INK4 family) may increase phosphorylation of Rb, and inhibit Rb function. In some embodiments, the agents described herein may also decrease the expression of ARF in cardiac cells. In addition, agents may also include transcriptional repressors of ARF, transcriptional activators of Mdm2, or agents that increase the levels of Mdm2 expression, decrease expression levels of p53, or increase the degradation of p53. Furthermore, the agent may also be an activator of cdk 4, an activator of cdk 6, an activator of E2F, an activator of atypical protein kinase C, an activator of Skp2, an activator of mdm2, an activator of MAP kinase, or any combination thereof. One skilled in the art would understand that agents that inhibit Rb pathway and/or ARF pathway may result in increased cell proliferation cardiac progenitor cells and help to heal ischemic injury.

The present disclosure provides methods for regenerating cardiac cells in vitro or in vivo. In some embodiments, the method includes contacting the cardiac cells with at least one agent that inhibits the function of retinoblastoma (Rb), alternate reading frame of Ink4a (ARF) protein, or any combination thereof. The cardiac cells comprise cardiac stem cells (CSCs), cardiac progenitor cells (CPCs), cardiomyocytes, or any combination thereof. In some embodiments, the agent may be any agent described herein that inhibit the function of Rb. In some embodiments, the agent may be any agent described herein that inhibit the function of ARF. Non-limiting examples of agents include a siRNA inhibitor, a shRNA inhibitor, an antisense nucleotide inhibitor, a peptide mimetic inhibitor, a small molecule, an antibody, a kinase that phosphorylates Rb, a transcriptional repressor of ARF, or any combination thereof. In addition, agents may also include transcriptional repressors of ARF, transcriptional activators of Mdm2, or agents that increase the levels of Mdm2 expression, decrease expression levels of p53, or increase the degradation of p53. Furthermore, the agent may also be an activator of cdk 4, an activator of cdk 6, an activator of E2F, an activator of atypical protein kinase C, an activator of Skp2, an activator of mdm2, an activator of MAP kinase, or any combination thereof. Further, the agent described herein may increase the phosphorylation of Rb in cardiac cells, and/or decrease the expression of ARF in cardiac cells.

In another embodiment, a method of regenerating cardiac cells in vitro or in vivo, comprises contacting a biological sample in vitro or administering to a patient suffering from a cardiac disease or disorder, a pharmaceutical composition wherein the composition comprises one or more agents which inhibit the expression, function or activity of retinoblastoma (Rb) and alternate reading frame of Ink4a (ARF). In some embodiments, mesenchymal stem cells (MSCs), cardiac stem cells (CSCs) or combinations of MSCs and CSCs are optionally administered to a subject or are co-cultured in a sample in vitro. In some embodiments, the generated cell comprise a phenotype identified having markers: HP3+/pRb$^{Ser608+}$/Gata4+//ARF-negative.

In some embodiments, methods are provided for predicting regeneration of cardiac cells in a subject treated for a heart disease. In some embodiments, the method may comprise obtaining a biological sample comprising cardiac cells from the subject; measuring phosphorylated retinoblastoma (pRb) levels in the biological sample; and comparing the phosphorylated retinoblastoma (pRb) levels in the biological sample to a baseline control, wherein an increased levels of pRb levels in the subject's biological sample when compared to the baseline control is predictive of the regeneration of the cardiac cells in the subject. In some embodiments, the measuring may comprise measuring and quantifying phosphorylation at Ser-608 of the retinoblastoma protein. The phosphorylated retinoblastoma (pRb) levels may be quantified by any known techniques in the art, such as immunohistochemical assays, Western blot assays, ELISA, biochemical enzymatic assays, or any combination thereof. In some embodiments, the cardiac cell may be a mature cardiomyocyte and/or a Gata4 positive (Gata4+) cardiac progenitor cell (CPC). Detection of an increased amount, expression or activity of pRb$^{ser608}$ is predictive of the regeneration of the cardiac cells in a subject. In embodiments, the pRb$^{ser608}$ is detected in compact ventricular walls of a subject's heart. At a cellular level, the pRb$^{ser608}$ is detected in mature cardiomyocytes and Gata4+ adult cardiac progenitor cells (CPCs). The increase in phosphorylation can be at least 10, 20, 30, 40, 50, 60, 70, 80, 90, 100, or 200% as compared to the baseline control. The baseline control can be, for example, levels of the phosphorylated protein in an untreated sample. The untreated sample can be from the patient being treated or can be from another patient.

Additionally, the baseline control can be from a pool of untreated samples such that the baseline control is an average obtain from a plurality of patients.

The present disclosure also provides methods to monitor and/or predict prognosis of a subject. In some embodiments, a method of identifying a subject treated for heart disease as a subject with a good prognosis may comprise obtaining a biological sample comprising cardiac cells from the subject; measuring phosphorylated retinoblastoma (pRb) levels in the biological sample; and comparing the phosphorylated retinoblastoma (pRb) levels in the biological sample to a baseline control, wherein an increased level of pRb in the subject's biological sample when compared to the baseline control identifies that subject as having a good prognosis. "Good prognosis" refers to a patient who is expected to recover. In some embodiments, the measuring comprises measuring phosphorylation at $Ser^{608}$ of the retinoblastoma protein. In some embodiments, the measuring may comprise measuring and quantifying phosphorylation at Ser-608 of the retinoblastoma protein. The phosphorylated retinoblastoma (pRb) levels may be quantified by any known techniques in the art, such as immunohistochemical assays, Western blot assays, ELISA, biochemical enzymatic assays, or any combination thereof. In some embodiments, the cardiac cell may be a mature cardiomyocyte and/or a Gata4 positive ($Gata4^+$) cardiac progenitor cell (CPC). In some embodiments, the subject may be treated with adult bone marrow-derived mesenchymal cells (MSCs), adult cardiac stem cells (CSCs), or any combination thereof. In some embodiments, an increase of at least 10, 20, 30, 40, 50, 60, 70, 80, 90, 100, or 200% as compared to the baseline control predicts a good prognosis. The baseline control can be, for example, levels of the phosphorylated protein in an untreated sample. The untreated sample can be from the patient being treated or has the heart disease or can be from another patient. Additionally, the baseline control can be from a pool of untreated samples such that the baseline control is an average obtain from a plurality of patients.

In some embodiments, the presence of phosphorylated Rb protein and the relative amounts as compared to a baseline control can be used to predict outcome or prognosis for the diseases discussed herein, including, but not limited to, myocarditis, Coronary Heart Disease, angina, Acute Coronary Syndrome, Aortic Aneurysm and Dissection, arrhythmias, Cardiomyopathy, Congenital Heart Disease, congestive heart failure or chronic heart failure, pericarditis, and the like.

In another embodiment, a method of monitoring a subject's recovery following treatment comprises obtaining a sample from a patient undergoing stem cell therapy, measuring expression, function or activity of retinoblastoma (Rb) as compared to a baseline control, wherein the retinoblastoma comprises a hyper-phosphorylated serine at amino acid position 608 ($pRb^{Ser608}$). In some embodiments, the treatment comprises administering to the subject: adult bone marrow-derived mesenchymal cells (MSCs), adult cardiac stem cells (CSCs), or combinations of MSCs and CSCs. In some embodiments, the $pRb^{ser608}$ expression, function or activity is increased in subjects treated with MSCs and CSCs as compared to treatment with CSCs or MSCs alone.

In another embodiment, a method of determining the rate of mitosis in a subject's cardiomyocytes comprises obtaining a biological sample from a subject undergoing treatment with stem cells; measuring expression, function or activity of retinoblastoma (Rb) in the biological sample as compared to a baseline control, wherein the retinoblastoma comprises a hyper-phosphorylated serine at amino acid position 608 ($pRb^{Ser608}$) and monitoring the subjects recovery following treatment. In some embodiments, the treatment comprises administering to the subject: adult bone marrow-derived mesenchymal cells (MSCs), adult cardiac stem cells (CSCs), or combinations of MSCs and CSCs. In some embodiments, the $pRb^{Ser608}$ expression, function or activity is increased in subjects treated with MSCs and CSCs as compared to treatment with CSCs or MSCs alone.

In other embodiments, MSC/CSC interaction induces inactivation of $pRb^{ser608}$ activity, function or expression. In another embodiment, MSC/CSC interaction induces inactivation of ARF activity, function or expression. In another embodiment, MSC/CSC interaction induces inactivation of $pRb^{ser608}$ and ARF activity, function or expression. In other embodiments, proliferation of serine-10 phosphorylated histone-H3/$pRb^{ser608}$ ($HP3^+$/$pRB^{ser608+}$) alternate reading frame of $Ink4a^{(-)}$ ($ARF^{(-)}$) cardiomyocytes, is increased as compared to a baseline control.

In some embodiments, biomarkers for cardiac progenitor cells are disclosed. In some embodiments, a biomarker comprises phosphorylated retinoblastoma (pRb) and alternate reading frame of Ink4a (ARF), mutants, variants or fragments thereof. In some embodiments, the marker pRb comprises a hyper-phosphorylated amino acid. In other embodiments, the hyper-phosphorylated amino acid is serine at amino acid position 608 ($pRb^{ser608}$). In some embodiments, detection of marker $pRB^{ser608}$ is determinative of $Gata4^+$ cardiac stem cells. In other embodiments, marker ARF is decreased as compared to a baseline control. The term "baseline control" means as it is used throughout the specification.

In some embodiments it is desirable to express the markers that comprise a biomarker, in a vector and in cells. The applications of such combinations are unlimited. The vectors and cells expressing the one or more biomolecules can be used in assays, kits, drug discovery, diagnostics, prognostics and the like. The cells can be stem cells isolated from the bone marrow as a progenitor cell, or cells obtained from any other source, such as for example, ATCC.

The biomarkers embodied herein, or cells expressing one or more markers can be used to screen for factors (such as solvents, small molecule drugs, peptides, oligonucleotides) or environmental conditions (such as culture conditions or manipulation) that affect the characteristics of such cells and their various progeny.

In some embodiments, a method of identifying a candidate agent to modulate Rb pathway in a cardiac progenitor cell may comprise contacting the candidate agent with a population of cardiac progenitor cells (CPCs); and comparing phosphorylated Rb levels in the population of cardiac progenitor cells contacted with the candidate agent to phosphorylated Rb levels in a population of CPCs not contacted with the candidate agent, wherein a difference in the phosphorylated Rb levels identifies the candidate agent as an agent that modulates the Rb pathway in the cardiac progenitor cell. The cardiac progenitor cells (CPCs) may be positive for phosphorylated $Rb^{ser608}$ ($pRb^{ser608}$), Gata4, or any combination thereof.

In some embodiments, a method of identifying a candidate agent is provided said method comprising: (a) contacting a biological sample from a patient with the candidate agent and determining the level of expression of one or more biomarkers described herein; (b) determining the level of phosphorylation, expression, function or activity of a corresponding biomarker or biomarkers in an aliquot of the biological sample not contacted with the candidate agent; (c) observing the effect of the candidate agent by comparing the level of phosphorylation, expression, function or activity of the biomarker or biomarkers in the aliquot of the biological sample contacted with the candidate agent and the level of phosphorylation, expression, function or activity of the corresponding biomarker or biomarkers in the aliquot of the biological sample not contacted with the candidate agent; and (d) identifying said agent from said observed effect, wherein an at least 1%, 2%, 5%, 10%, 20%, 30%, 40%, 50%, 60%, 70%, 80%, or 90% difference between the level of phosphorylation, expression, function or activity of the biomarker or combination of biomarker genes in the aliquot of the biological sample contacted with the candidate agent and the level of phosphorylation, expression, function or activity of the corresponding biomarker or combination of biomarker in the aliquot of the biological sample not contacted with the candidate agent is an indication of an effect of the candidate agent.

In some embodiments, a candidate agent derived by the methods described herein are provided.

In some embodiments, a pharmaceutical preparation comprising an agent according to the embodiments described herein are provided.

In some embodiments, a method of producing a drug comprising the steps of (i) synthesizing the candidate agent identified in step (c) above or an analog or derivative thereof in an amount sufficient to provide said drug in a therapeutically effective amount to a subject; and/or (ii) combining the drug candidate the candidate agent identified in step (c) above or an analog or derivative thereof with a pharmaceutically acceptable carrier.

Other screening applications relate to the testing of pharmaceutical compounds for their effect on cardiac muscle tissue maintenance or repair. Screening may be done either because the compound is designed to have a pharmacological effect on the cells, or because a compound designed to have effects elsewhere may have unintended side effects on cells of this tissue type. The screening can be conducted using any of the stem cells or terminally differentiated cells.

In some embodiments, the markers are useful for the identification of new drugs in the treatment of cardiovascular diseases and disorders.

In some embodiments, the markers would verify whether a patient's treatment is progressing. For example, the amount, activity or expression of $pRb^{ser608}$ may change during the course of treatment and reflect normal controls.

Small molecule test compounds or candidate therapeutic compounds can initially be members of an organic or inorganic chemical library. As used herein, "small molecules" refers to small organic or inorganic molecules of molecular weight below about 3,000 Daltons. The small molecules can be natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, Solid-Supported Combinatorial and Parallel Synthesis of Small-Molecular-Weight Compound Libraries, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio., 1:60 (1997). In addition, a number of small molecule libraries are commercially available.

Particular screening applications disclosed herein relate to the testing of pharmaceutical compounds in drug research. The reader is referred generally to the standard textbook "In vitro Methods in Pharmaceutical Research", Academic Press, 1997, and U.S. Pat. No. 5,030,015). Assessment of the activity of candidate pharmaceutical compounds generally involves administering a candidate compound, determining any change in the morphology, marker phenotype and expression, or metabolic activity of the cells and function of the cells that is attributable to the compound (compared with untreated cells or cells treated with an inert compound), and then correlating the effect of the compound with the observed change.

The screening may be done, for example, either because the compound is designed to have a pharmacological effect on certain cell types, or because a compound designed to have effects elsewhere may have unintended side effects. Two or more drugs can be tested in combination (by combining with the cells either simultaneously or sequentially), to detect possible drug-drug interaction effects. In some applications, compounds are screened initially for potential toxicity (Castell et al., pp. 375-410 in "In vitro Methods in Pharmaceutical Research," Academic Press, 1997). Cytotoxicity can be determined in the first instance by the effect on cell viability, survival, morphology, and expression or release of certain markers, receptors or enzymes. Effects of a drug on chromosomal DNA can be especially at unscheduled times in the cell cycle, or above the level required for cell replication, is consistent with a drug effect. Unwanted effects can also include unusual rates of sister chromatid exchange, determined by metaphase spread. The reader is referred to A. Vickers (PP 375-410 in "In vitro Methods in Pharmaceutical Research," Academic Press, 1997) for further elaboration.

Examples of methods include, but are not limited to, the standard textbook In vitro Methods in Pharmaceutical Research, Academic Press, 1997 and U.S. Pat. No. 5,030,015. Assessment of the activity of candidate pharmaceutical compounds generally involves combining the cells with the candidate compound, either alone or in combination with other drugs. The investigator determines any change in the morphology, marker phenotype, or functional activity of the cells that is attributable to the compound (compared with untreated cells or cells treated with an inert compound), and then correlates the effect of the compound with the observed change.

Cytotoxicity can be determined in the first instance by the effect on cell viability, survival, morphology, and the expression of certain markers and receptors. Effects of a drug on chromosomal DNA can be determined by measuring DNA synthesis or repair. [$^3$H]-thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to A. Vickers (pp 375-410 in In vitro Methods in Pharmaceutical Research, Academic Press, 1997) for further elaboration.

Effect of cell function can be assessed using any standard assay to observe phenotype or activity of cardiomyocytes, such as marker expression, receptor binding, contractile activity, or electrophysiology, either in cell culture or in vivo. Pharmaceutical candidates can also be tested for their effect on contractile activity, such as whether they increase or decrease the extent or frequency of contraction. Where an effect is observed, the concentration of the compound can be titrated to determine the median effective dose ($ED_{50}$).

An agent that inhibits the function of Rb and/or ARF may be formulated as a pharmaceutical composition or medicament. Pharmaceutical compositions adapted for direct administration include, without limitation, lyophilized powders or aqueous or non-aqueous sterile injectable solutions or suspensions, which may further contain antioxidants, buffers, bacteriostats and solutes that render the compositions substantially isotonic with the blood of an intended recipient. Other components that may be present in such compositions include water, alcohols, polyols, glycerin and vegetable oils, for example. Extemporaneous injection solutions and suspensions may be prepared from sterile powders, granules and tablets. The agents may be supplied, for example but not by way of limitation, as a lyophilized powder which is reconstituted with sterile water or saline prior to administration to the patient.

Pharmaceutical compositions may comprise a pharmaceutically acceptable carrier. Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1(2,3-dioleyloxy) propyl)N, N,N-trimethylammonium chloride (DOTMA), diolesyl-phosphotidyl-ethanolamine (DOPE), and liposomes. Such compositions should contain a therapeutically effective amount of the compound, together with a suitable amount of carrier so as to provide the form for direct administration to the patient.

The composition may be in the form of a pharmaceutically acceptable salt which includes, without limitation, those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethyl-amino ethanol, histidine, procaine, etc.

In various embodiments, the pharmaceutical composition is directly administered to the area of the injury, such as to the cardiac tissue by, for example, local infusion during surgery, topical application (e.g., in conjunction with a wound dressing after surgery), injection, means of a catheter, means of a suppository, or means of an implant. An implant can be of a porous, non-porous, or gelatinous material, including membranes, such as sialastic membranes, or fibers. Suppositories generally contain active ingredients in the range of 0.5% to 10% by weight.

In other embodiments, a controlled release system can be placed in proximity of the target site. For example, a micropump may deliver controlled doses directly into the area of the target site, such as to the cardiac tissue, thereby finely regulating the timing and concentration of the pharmaceutical composition.

In accordance some embodiments, the agent that inhibits the function of Rb and/or ARF is delivered to the patient by direct administration. Accordingly, the agent may be administered, without limitation, by one or more direct injections into the target site, by continuous or discontinuous perfusion into the target site, by introduction of a reservoir of the agent, by introduction of a slow-release apparatus into the target site, by introduction of a slow-release formulation into the target site, and/or by direct application onto the target site. By the mode of administration into the target site, introduction of the agent into a blood vessel or lymphatic vessel that substantially directly flows into the area of the target site, is also contemplated. In each case, the pharmaceutical composition is administered in at least an amount sufficient to achieve the endpoint, and if necessary, comprises a pharmaceutically acceptable carrier.

In some embodiments, the pharmaceutical carrier may include, without limitation, binders, coating, disintegrants, fillers, diluents, flavors, colors, lubricants, glidants, preservatives, sorbents, sweeteners, conjugated linoleic acid (CLA), gelatin, beeswax, purified water, glycerol, any type of oil, including, without limitation, fish oil or soybean oil, or the like. Pharmaceutical compositions of the peptides/compounds also can comprise suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols.

The agents disclosed herein can be administered, for example, in the conventional manner by any route where they are active. Administration can be systemic, parenteral, topical, or oral. For example, administration can be, but is not limited to, parenteral, subcutaneous, intravenous, intramuscular, intraperitoneal, transdermal, oral, buccal, or ocular routes, or intravaginally, by inhalation, by depot injections, or by implants. Thus, modes of administration for the agents (either alone or in combination with other pharmaceuticals) can be, but are not limited to, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal forms such as patches and creams.

For oral administration, the agents can be formulated readily by combining these agents with pharmaceutically acceptable carriers well known in the art. Such carriers enable the agents, compounds, cells, etc. to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active peptides/compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active peptides/compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of, e.g., tablets or lozenges formulated in a conventional manner.

For administration by inhalation, the compositions for use are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the peptides/compound and a suitable powder base such as lactose or starch.

The compositions can also be formulated in rectal compositions such as suppositories or retention enemas, e.g., containing conventional suppository bases such as cocoa butter or other glycerides.

In addition to the formulations described previously, the compositions can also be formulated as a depot preparation. Such long acting formulations can be administered by implantation (for example subcutaneously or intramuscularly) or by intramuscular injection.

Depot injections can be administered at about 1 to about 6 months or longer intervals. Thus, for example, the peptides/compounds can be formulated with suitable polymeric or hydrophobic materials (for example as an emulsion in an acceptable oil) or ion exchange resins, or as sparingly soluble derivatives, for example, as a sparingly soluble salt.

In transdermal administration, the compositions, for example, can be applied to a plaster, or can be applied by transdermal, therapeutic systems that are consequently supplied to the organism.

The compositions can also be administered in combination with other active ingredients, such as, for example, adjuvants, protease inhibitors, or other compatible drugs or compounds where such combination is seen to be desirable or advantageous in achieving the desired effects of the methods described herein.

In some embodiments, the disintegrant component comprises one or more of croscarmellose sodium, carmellose calcium, crospovidone, alginic acid, sodium alginate, potassium alginate, calcium alginate, an ion exchange resin, an effervescent system based on food acids and an alkaline carbonate component, clay, talc, starch, pregelatinized starch, sodium starch glycolate, cellulose floc, carboxymethylcellulose, hydroxypropylcellulose, calcium silicate, a metal carbonate, sodium bicarbonate, calcium citrate, or calcium phosphate.

In some embodiments, the diluent component comprises one or more of mannitol, lactose, sucrose, maltodextrin, sorbitol, xylitol, powdered cellulose, microcrystalline cellulose, carboxymethylcellulose, carboxyethylcellulose, methylcellulose, ethylcellulose, hydroxyethylcellulose, methylhydroxyethylcellulose, starch, sodium starch glycolate, pregelatinized starch, a calcium phosphate, a metal carbonate, a metal oxide, or a metal aluminosilicate.

In some embodiments, the optional lubricant component, when present, comprises one or more of stearic acid, metallic stearate, sodium stearyl fumarate, fatty acid, fatty alcohol, fatty acid ester, glyceryl behenate, mineral oil, vegetable oil, paraffin, leucine, silica, silicic acid, talc, propylene glycol fatty acid ester, polyethoxylated castor oil, polyethylene glycol, polypropylene glycol, polyalkylene glycol, polyoxyethylene-glycerol fatty ester, polyoxyethylene fatty alcohol ether, polyethoxylated sterol, polyethoxylated castor oil, polyethoxylated vegetable oil, or sodium chloride.

As discussed herein various techniques can be used to identify or detect certain markers. The following are non-limiting examples of such techniques. In general, using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes that have potential to be expressed in certain disease states may be arrayed on a solid support. Hybridization of a labeled probe with a particular array member indicates that the sample from which the probe was derived expresses that gene. Differential gene expression analysis of disease tissue can provide valuable information. Microarray technology utilizes nucleic acid hybridization techniques and computing technology to evaluate the mRNA expression profile of thousands of genes within a single experiment. (see, e.g., WO 01/75166 published Oct. 11, 2001; (See, for example, U.S. Pat. No. 5,700,637, U.S. Pat. No. 5,445,934, and U.S. Pat. No. 5,807,522, Lockart, *Nature Biotechnology*, 14:1675-1680 (1996); Cheung, V. G. et al., *Nature Genetics* 21(Suppl):15-19 (1999) for a discussion of array fabrication). DNA microarrays are miniature arrays containing gene fragments that are either synthesized directly onto or spotted onto glass or other substrates. Thousands of genes are usually represented in a single array. A typical microarray experiment involves the following steps: 1) preparation of fluorescently labeled target from RNA isolated from the sample, 2) hybridization of the labeled target to the microarray, 3) washing, staining, and scanning of the array, 4) analysis of the scanned image and 5) generation of gene expression profiles. Currently two main types of DNA microarrays are being used: oligonucleotide (usually 25 to 70 mers) arrays and gene expression arrays containing PCR products prepared from cDNAs. In forming an array, oligonucleotides can be either prefabricated and spotted to the surface or directly synthesized on to the surface (in situ). The Affymetrix GeneChip™ system is a commercially available microarray system which comprises arrays fabricated by direct synthesis of oligonucleotides on a glass surface.

Probes and gene arrays can also be used. Oligonucleotides, usually 25 mers, are directly synthesized onto a glass wafer by a combination of semiconductor-based photolithography and solid phase chemical synthesis technologies. Each array can contain up to 400,000 different oligonucleotides and each oligonucleotide is present in millions of copies. Since oligonucleotide probes are synthesized in known locations on the array, the hybridization patterns and signal intensities can be interpreted in terms of gene identity and relative expression levels by the Affymetrix Microarray Suite software. Each gene is represented on the array by a series of different oligonucleotide probes. Each probe pair consists of a perfect match oligonucleotide and a mismatch oligonucleotide. The perfect match probe has a sequence exactly complimentary to the particular gene and thus measures the expression of the gene. The mismatch probe differs from the perfect match probe by a single base substitution at the center base position, disturbing the binding of the target gene transcript. This helps to determine the background and nonspecific hybridization that contributes to the signal measured for the perfect match oligonucleotide. The Microarray Suite software subtracts the hybridization intensities of the mismatch probes from those of the perfect match probes to determine the absolute or specific intensity value for each probe set. Probes are chosen based on current information from GenBank and other nucleotide repositories. The sequences are believed to recognize unique regions of the 3' end of the gene. A GeneChip Hybridization Oven ("rotisserie" oven) is used to carry out the hybridization of up to 64 arrays at one time. The fluidics station performs washing and staining of the probe arrays. It is completely automated and contains four modules, with each module holding one probe array. Each module is controlled independently through Microarray Suite software using preprogrammed fluidics protocols. The scanner is a confocal laser fluorescence scanner which measures fluorescence intensity emitted by the labeled cRNA bound to the probe arrays. The computer workstation with Microarray Suite software controls the fluidics station and the scanner. Microarray Suite software can control up to eight fluidics stations using preprogrammed hybridization, wash, and stain protocols for the probe array. The software also acquires and converts hybridization intensity data into a presence/absence call for each gene using appropriate algorithms. Finally, the software detects changes in gene expression between experiments by comparison analysis and formats the output into .txt files, which can be used with other software programs for further data analysis.

The expression of a selected biomarker may also be assessed by examining gene deletion or gene amplification. Gene deletion or amplification may be measured by any one of a wide variety of protocols known in the art, for example, by conventional Southern blotting, Northern blotting to quantitate the transcription of mRNA (Thomas, *Proc. Natl. Acad. Sci.* USA, 77:5201-5205 (1980)), dot blotting (DNA analysis), or in situ hybridization (e.g., FISH), using an appropriately labeled probe, cytogenetic methods or comparative genomic hybridization (CGH) using an appropriately labeled probe.

In some embodiments, a polypeptide corresponding to a marker is detected. In some embodiments, an antibody or aptamer capable of binding to a polypeptide corresponding to a marker described herein, or an antibody with a detectable label, is used. Antibodies can be polyclonal or monoclonal. An intact antibody, or a fragment thereof, e.g., Fab or F(ab')$_2$ can be also used.

Proteins from individuals can also be isolated using techniques that are well-known to those of skill in the art. The protein isolation methods employed can, e.g., be such as those described in Harlow & Lane (1988), supra. A variety of formats can be employed to determine whether a sample contains a protein that binds to a given antibody. Expression of various biomarkers in a sample can be analyzed by a number of methodologies, many of which are known in the art and understood by the skilled artisan, including but not limited to, immunohistochemical and/or Western analysis, quantitative blood based assays (as for example Serum ELISA) (to examine, for example, levels of protein expression), biochemical enzymatic activity assays, in situ hybridization, Northern analysis and/or PCR analysis of mRNAs, as well as any one of the wide variety of assays that can be performed by gene and/or tissue array analysis. Typical protocols for evaluating the status of genes and gene products are found, for example in Ausubel et al. eds., 1995, Current Protocols In Molecular Biology, Units 2 (Northern Blotting), 4 (Southern Blotting), 15 (Immunoblotting) and 18 (PCR Analysis). A skilled artisan can readily adapt known protein/antibody detection methods for use in determining whether cells express a marker and/or the relative concentration of that specific polypeptide expression product in blood or other body tissues.

In some embodiments, a sample may be contacted with an antibody specific for said biomarker under conditions sufficient for an antibody-biomarker complex to form, and then detecting said complex. The presence of the biomarker may be detected in a number of ways, such as by Western blotting and ELISA procedures for assaying a wide variety of tissues and samples, including plasma or serum. A wide range of immunoassay techniques using such an assay format are available, see, e.g., U.S. Pat. Nos. 4,016,043, 4,424,279 and 4,018,653. These include both single-site and two-site or "sandwich" assays of the non-competitive types, as well as in the traditional competitive binding assays. These assays also include direct binding of a labeled antibody to a target biomarker.

Sandwich assays are commonly used assays. A number of variations of the sandwich assay technique exist, and all are intended to be encompassed by the present disclosure. Briefly, in a typical forward assay, an unlabeled antibody is immobilized on a solid substrate, and the sample to be tested brought into contact with the bound molecule. After a suitable period of incubation, for a period of time sufficient to allow formation of an antibody-antigen complex, a second antibody specific to the antigen, labeled with a reporter molecule capable of producing a detectable signal is then added and incubated, allowing time sufficient for the formation of another complex of antibody-antigen-labeled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of biomarker.

Variations on the forward assay include a simultaneous assay, in which both sample and labeled antibody are added simultaneously to the bound antibody. These techniques are well known to those skilled in the art, including any minor variations as will be readily apparent. In a typical forward sandwich assay, a first antibody having specificity for the biomarker is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-40 minutes or overnight if more convenient) and under suitable conditions (e.g. from room temperature to 40° C. such as between 25° C. and 32° C. inclusive) to allow binding of any subunit present in the antibody. Following the incubation period, the antibody subunit solid phase is washed and dried and incubated with a second antibody specific for a portion of the biomarker. The second antibody is linked to a reporter molecule which is used to indicate the binding of the second antibody to the molecular marker.

In some embodiments, a method involves immobilizing the target biomarkers in the sample and then exposing the immobilized target to specific antibody which may or may not be labeled with a reporter molecule can be used. Depending on the amount of target and the strength of the reporter molecule signal, a bound target may be detectable by direct labeling with the antibody. Alternatively, a second labeled antibody, specific to the first antibody is exposed to the target-first antibody complex to form a target-first antibody-second antibody tertiary complex. The complex is detected by the signal emitted by the reporter molecule. By "reporter molecule", as used in the present specification, is meant a molecule which, by its chemical nature, provides an analytically identifiable signal which allows the detection of antigen-bound antibody. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan.

Commonly used enzymes include horseradish peroxidase, glucose oxidase, -galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labeled antibody is added to the first antibody-molecular marker complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of biomarker which was present in the sample. Alternately, fluorescent compounds, such as fluorescein and rhodamine, may be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic color visually detectable with a light microscope. As in the EIA, the fluorescent labeled antibody is allowed to bind to the first antibody-molecular marker complex. After washing off the unbound reagent, the remaining tertiary complex is then exposed to the light of the appropriate wavelength, the fluorescence observed indicates the presence of the molecular marker of interest. Immunofluorescence and EIA techniques are both very well established in the art. However, other reporter molecules, such as radioisotope, chemiluminescent or bioluminescent molecules, may also be employed.

Methods described herein can also include protocols which examine the presence and/or expression of mRNAs, in a tissue or cell sample. Methods for the evaluation of mRNAs in cells are well known and include, for example, hybridization assays using complementary DNA probes (such as in situ hybridization using labeled riboprobes, Northern blot and related techniques) and various nucleic acid amplification assays (such as RT-PCR and other amplification type detection methods, such as, for example, branched DNA, SISBA, TMA and the like).

In some embodiments, the level of mRNA corresponding to the marker can be determined both by in situ and by in vitro formats in a biological sample using methods known in the art. Many expression detection methods use isolated RNA. For in vitro methods, any RNA isolation technique that does not select against the isolation of mRNA can be utilized for the purification of RNA from cells. See, e.g., Ausubel et al., Ed., Curr. Prot. Mol. Biol., John Wiley & Sons, NY (1987-1999). Additionally, large numbers of tissue samples can readily be processed using techniques well-known to those of skill in the art, such as, e.g., the single-step RNA isolation process of U.S. Pat. No. 4,843,155. The isolated mRNA can be used in hybridization or amplification assays that include, but are not limited to, Southern or Northern analyses, PCR analyses and probe arrays. In some embodiments, a method for the detection of mRNA levels comprises contacting the isolated mRNA with a nucleic acid molecule (probe) that can hybridize to the mRNA encoded by the gene being detected. The nucleic acid probe can be, e.g., a full-length cDNA, or a portion thereof, such as an oligonucleotide of at least 7, 15, 30, 50, 100, 250 or 500 nucleotides in length and sufficient to specifically hybridize under stringent conditions to a mRNA encoding a marker described herein.

In some embodiments, the mRNA is immobilized on a solid surface and contacted with a probe, for example, by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the markers described herein.

For in situ methods, mRNA does not need to be isolated form the cells prior to detection. In such methods, a cell or tissue sample is prepared/processed using known histological methods. The sample is then immobilized on a support, typically a glass slide, and then contacted with a probe that can hybridize to mRNA that encodes the marker.

As an alternative to making determinations based on the absolute expression level of the marker, determinations may be based on the normalized expression level of the marker. Expression levels are normalized by correcting the absolute expression level of a marker by comparing its expression to the expression of a gene that is not a marker, e.g., a housekeeping gene that is constitutively expressed. Suitable genes for normalization include housekeeping genes, such as the actin gene or epithelial cell-specific genes. This normalization allows the comparison of the expression level in one sample, e.g., a patient sample, to another sample or between samples from different sources.

Alternatively, the expression level can be provided as a relative expression level. To determine a relative expression level of a marker, the level of expression of the marker is determined for 10 or more samples of normal versus disease biological samples, or 50 or more samples, prior to the determination of the expression level for the sample in question. The mean expression level of each of the genes assayed in the larger number of samples is determined and this is used as a baseline expression level for the marker. The expression level of the marker determined for the test sample (absolute level of expression) is then divided by the mean expression value obtained for that marker. This provides a relative expression level.

The choice of the cell source is dependent on the use of the relative expression level. Using expression found in normal tissues as a mean expression score aids in validating whether the marker assayed is specific (versus normal cells).

In addition, as more data is accumulated, the mean expression value can be revised, providing improved relative expression values based on accumulated data.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art."

EXAMPLES

While various embodiments have been described above, it should be understood that they have been presented by way of example only, and not limitation. Numerous changes to the disclosed embodiments can be made in accordance with the disclosure herein without departing from the spirit or scope of the embodiments. Thus, the breadth and scope of the claims should not be limited without an express and explicit disclaimer.

Example 1: Function of Rb in Cardiomyogenisis

Methods

Briefly, hCSCs and hMSCs, in combination or alone, were administered to swine hearts following myocardial infarction (MI) and cardiac pRb activity was assessed. Stem cell transplantation was performed 2 weeks after MI, as described (Williams A R, Hatzistergos K E, et al. Enhanced effect of human cardiac stem cells and bone marrow mesenchymal stem cells to reduce infarct size and restore cardiac function after myocardial infarction. *Circulation.* 2013 Jan. 15; 127(2):213-23 (Epub 2012 Dec. 5)). The following groups were studied: 200M hMSCs, 1M hCSCs, 200M hMSC plus 1M hCSC or placebo (n=3 each). All human cells were obtained from unrelated coded donors, using previously described methods (Hare J M, et al. *JAMA* 2012 Nov. 6; 1-11; Bolli R, et al. *Lancet* 2011 Nov. 26; 378(9806):1847-57).

All animal protocols were reviewed and approved by the University of Miami Institutional Animal Use and Care Committee.

Myocardial Infarction

The porcine model of MI was performed as recently described (Hatzistergos K E et al. Bone Marrow Mesenchymal Stem Cells Stimulate Cardiac Stem Cell Proliferation and Differentiation. *Circ Res* 2010 July 29; Williams A R, et al. Enhanced effect of human cardiac stem cells and bone marrow mesenchymal stem cells to reduce infarct size and restore cardiac function after myocardial infarction. *Circulation.* In press 2012). Briefly, Yorkshire swine (35-40 kg, n=22) underwent a closed-chest, ischemia-reperfusion protocol to generate a model of anterior wall MI. Using angioplasty techniques, balloon occlusion of the left anterior descending coronary artery immediately beyond the first diagonal branch for 90 minutes was performed to induce MI and full reperfusion was confirmed by angiography after balloon deflation.

Cell Isolation and Culturing

Explanted cardiac tissue was harvested following IRB approval and informed consent, from the core of apical tissue removed during implantation of a left ventricle assist device (LVAD) in a single human male donor. CSCs expressing c-kit were isolated from the enzymatic dissociated myocardial sample using magnetic microbeads coupled to anti-human CD117 antibody (Miltenyi Biotech), as previously described (Bolli R, et al. *Lancet* 2011 Nov. 26; 378(9806):1847-57). After dissociation, cells were plated at a high density, amplified, harvested, and cryopreserved.

For hMSCs isolation, a bone marrow (BM) aspirate was obtained from the iliac crest of a human male donor. Human MSCs were isolated from other BM cells by Ficoll density centrifugation and plastic adherence as previously described (Hare J M, et al. *JAMA* 2012 Nov. 6; 1-11); hMSCs were amplified, harvested, and cryopreserved. On the morning of stem cell injection, cells were thawed, washed and resuspended in phosphate buffered saline (PBS). For hMSC alone injections (n=3), 200 million hMSCs were suspended in 6 ml of PBS, and for hCSC alone injection (n=3), 1 million hCSCs were suspended in 3 ml of PBS. For the combined injections (n=3), 1 million hCSCs and 200 million hMSCs were suspended in a total volume of 6 ml of PBS and mixed before injection. For placebo injections (n=3), 6 ml of PBS was administered. All cells or placebo injections were divided into 10 equal volume aliquots and injected transepicardially with a 27 gauge needle.

Cardiac Magnetic Resonance Imaging

CMR studies were conducted on a Siemens Trio 3T Tim (Erlangen, Germany) scanner with Syngo MR software using a 16-channel body surface coil with ECG gating and short breath-hold acquisition. The QMass Software (Medis, Leiden, Netherlands) was employed to calculate scar size.

Cell Transplantation

The xenogeneic model of cell therapy was performed as previously described (Williams A R, et al. *Circulation.* In press 2012). At 14 days post-MI, animals underwent thoracoscopy guided direct transepicardial stem cell (n=9) or placebo injection (n=3). Coronary angiography from MI induction and delayed enhancement CMR images were reviewed to define coronary anatomy and infarct extent. A left mini-thoracotomy was created with a small 4-5 cm incision in the 5th anterior/lateral intercostal space, and the left plural cavity entered under direct visualization. A 5 mm port was placed in the 6th or 7th intercostal space, and a 5 mm endoscope (Karl Storz, Tuttlingen, Germany) inserted into the left chest cavity. The pericardium was opened and infarct area identified by wall motion abnormalities and correlation with coronary anatomy. A curved 27-gauge needle was inserted tangentially into the myocardium and 10 separate injections administered to the infarct border zone. Adequate hemostasis of needle puncture sites was achieved with gentle finger pressure. A 12-French chest tube was inserted into the left pleural cavity via the port incision, and tunneled through the chest wall. All incisions were closed and the chest tube placed to −20 cm of underwater suction to evacuate the pnuemothorax. Fluoroscopy was done to confirm lung expansion and the chest tube removed prior to extubation. Animals were recovered and provided adequate post-operative analgesia with a transdermal fentanyl patch (75 mcg/hr) for 3 days and bupernorpherine (0.03 mg/kg IM) immediately post-procedure. All animals were euthanatized at 6 weeks post MI.

Immunohistochemistry

Immunofluorescence analyses and confocal microscopy were performed in 5 μm-thick, formalin-fixed, paraffin-embedded tissue sections as previously described (Hatzistergos K E, et al. *Circ Res* 2010; 107(7): 913-922). Briefly, after deparaffinizing and rehydrating the tissue sections, antigen unmasking was performed by microwaving the slides for 20 min in citrate buffer Solution, pH=6 (Dako). Sections were blocked for 1 h with 10% normal donkey serum (Millipore) followed by overnight incubation at 4° C. with the primary antibody. The following antibodies were used: anti-porcine C-kit (mouse monoclonal), anti-human c-kit (rabbit polyclonal; DAKO), tropomyosin (mouse monoclonal; Abcam), ser-608 pRb (Goat polyclonal; Santa Cruz Biotechnologies), ARF (rabbit polyclonals; Novus Biologicals and Abcam), GATA-4 (Rabbit and goat polyclonals; Santa Cruz Biotechnologies), WT1 (rabbit polyclonal; Santa Cruz Biotechnologies), cardiac myosin light chain-2v (Rabbit polyclonal; Novus biological), Laminin (goat polyclonal; Abcam) and ser-10 phosphorylated histone-H3 (mouse monoclonal; Abcam). The next day, antibodies were visualized by incubating the sections for 1 h at 37° C. with FITC, Cy3 or Cy5-conjugated F(ab')2 fragments of affinity-purified secondary antibodies (Jackson Immunoresearch). Slides were counterstained with DAPI, mounted with ProLong Antifade Gold reagent (Life Technologies) and stored at 4° C. until further examination. Microscopic evaluations and image acquisitions were performed with a Zeiss LSM-710 Confocal Microscope (Carl Zeiss). The Carl Zeiss ZEN software (2009, light edition) was used for analyses.

Statistical Analysis

All values are expressed as means (+/−SEM). Differences in $pRb^{ser608}$ between groups were calculated with a Kruskal-Wallis ANOVA. A paired Student's t-test was employed for calculating differences in myocyte cross-sectional areas. Linear regression analysis was used to test the regression of cell numbers with cMRI-based scar size reductions. Graph-Pad Prism (Version 4.03, La Jolla, Calif.) was used to analyze all data and plot graphs. A p-value of less than 0.05 was considered statistically significant.

Results $pRb^{Ser608}$ Reflects Host Regenerative Cardiac Cells and is Enhanced by MSCs/CSCs Interactions.

Because hyper-phosphorylation of pRb at Ser-608 inhibits pRb activity and is a hallmark of regeneration in injured adult newt hearts, we tested whether $pRb^{ser608}$ participates in mammalian myocardial regenerative activity following cell-based therapy. However, there was no expectation of success in whether pRb would work in the same manner in mammalian heart muscle because the newt physiology and regenerative systems are significantly different. For example, Rb in human stem cells and disease pathways operates in very different ways, when compared to stem cells and disease pathways in other species. Therefore, any experimental information regarding the mechanisms by which Rb controls cell-cycle and cell-fate decisions in mice or newts does not necessarily mean that these mechanisms are operative in humans. In addition, ARF has no homologues in lower vertebrates, such as the newt and the zebrafish, which display regenerative capacity. For example, a newt can regenerate a limb after amputation, whereas this process does not occur in humans. Thus, although regeneration occurs in newts and neonatal mice, through various signaling pathways, this phenomenon in the adult mammal is non-obvious. Therefore, it was uncertain whether pRb would have a role in regenerating heart muscle. Therefore, tests were performed as to whether $pRb^{Ser608}$ was absent from the compact myocardial ventricular wall in normal myocardium and was restricted to epicardial and endocardial cells in healthy porcine myocardium (FIG. 6). Following ischemic injury, its expression increased substantially in the compact ventricular myocardial wall where $pRb^{Ser608}$ was identified in both mature cardiomyocytes and Gata4+ CPCs (immature cells expressing Gata4), but not in cells of extracardiac lineage (FIGS. 1A, 1B).

To assess the impact of cell therapy on endogenous cell inactivation of pRb, quantified $pRb^{Ser608+}$ CPCs were quantified in the four cell treatment groups. Compared to placebo, pRb was increased in abundance following stem cell therapy (p<0.0001) (FIG. 1 c,d). Relative to hMSCs, hCSCs induced $pRb^{Ser608}$ in host CPCs to a greater extent, both in the infarct and border zones. When hCSCs and hMSCs were coinjected, this effect was enhanced by ~1.5-fold compared to each cell type alone and by ~3 fold compared to placebo (p<0.0001) (FIGS. 1C, 1D).

Abundance of Host Progenitor Cells

To determine whether pRbser608 participates in cell-cycle or cell-fate decisions in endogenous CPCs, differences in cells expressing several markers known to identify adult CPCs were quantified, including Wt1+, c-kit+ and Gata4+. No differences were found in the myocardial abundance in Wt1+, c-kit+ or Gata4+ CPCs between the four groups at 4 weeks. Furthermore, although co-localization with the mitotic marker serine-10 phosphorylated histone-H3 (HP3) revealed a substantial number of these CPCs undergoing cell division, the differences in replicating CPCs between groups also was not affected by the different cell therapy (p=0.08 and p=0.36 in infarct and border zones respectively) (FIG. 2). Thus, similar to the role of pRb in embryonic stem cell-derived CPCs, these findings provide evidence that pRbSer608 determines lineage commitment rather than proliferative activity in adult Gata4+ CPCs (FIG. 2).

$pRb^{Ser608}$ in Host Cardiomyocytes

Investigated next was the role of $pRb^{Ser608}$ in endogenous cardiomyocytes. Confocal immunofluorescence demonstrated that neither hCSCs nor hMSCs alone influenced levels of $pRb^{Ser608}$ in host cardiomyocytes FIGS. 1E, 1F). However, combined engraftment of hMSCs and hCSCs resulted in major inactivation (~60% of the cardiomyocytes in infarct and border zones) of pRb as evidenced by $pRb^{Ser608+}$ (FIGS. 1E, 1F). Because pRbSer608 expression confers proliferative activity in adult newt cardiomyocytes, the rates of mitosis were analyzed in cardiomyocytes between groups. Engraftment of hCSCs or hMSCs alone did not increase the rates of cardiomyocyte proliferation 4 weeks after therapy (FIG. 3). However, combined engraftment of hMSCs and hCSCs, increased the number of HP3+ cardiomyocytes within the infarcted zone by 3-fold compared to the hMSC-treated animals and by 10-fold compared to hCSC and placebo treated groups (p<0.0001) (FIG. 3). In infarct border zones, this potentiation was of greater magnitude: there was a 6-fold increase in the numbers of HP3+ cardiomyocytes compared to the hMSC and hCSC therapies alone, and a 46-fold increase relative to placebo (p<0.0001) (FIG. 3). Additionally, morphometric analysis illustrated that the cross-sectional areas of these newly formed cardiomyocytes were significantly smaller compared to cardiomyocytes in the placebo treated group (p<0.05), providing evidence that they are transient amplifying progeny of host CPCs19 (FIG. 7). The abundance of $pRb^{Ser608}$ correlated significantly with the numbers of cardiomyocytes in mitosis (FIG. 8A), further supporting the conclusion that hMSCs/hCSCs interactions induce $pRb^{Ser608}$ inactivation and the subsequent regulation of cardiomyocyte cell-cycle activity.

MSCs/CSCs Interactions Yield pRbSer608+/ARF(−) Transient Amplifying Cardiomyocytes There were fewer mitotic cardiomyocytes compared to $pRb^{Ser608+}$ cardiomyocytes, indicating that, compared to the newt, $pRb^{Ser608}$ inactivation was not sufficient to trigger massive cell cycle re-entry. To address the possibility that ARF suppresses adult $pRb^{Ser608}$ cardiac myocytes from progressing to mitosis, ARF myocardial expression was analyzed. It was found that ARF was expressed in the majority of cardiomyocytes, including the $pRb^{Ser608+}$ cardiomyocytes, of all groups (FIG. 3, FIGS. 9A-9H). However, in swine treated with the combination of hMSCs and hCSCs, ARF was significantly repressed in ~20% of pRb$^{Ser608+}$ cardiomyocytes (FIG. 3). Additionally, although transient inactivation of ARF is necessary for progression from G phase to mitosis, animals treated with the combination of hMSCs and hCSCs contained mitotically dividing cardiomyocytes with an HP3$^+$/pRb$^{Ser608+}$ but ARF-negative phenotype, providing evidence that the regeneration of mature cardiomyocytes with broadened proliferative potentials within the injured porcine heart (FIG. 3, FIG. 10).

Importantly, the abundance of pRb$^{Ser608+}$/ARF-negative cells correlated with the degree of cardiomyocyte mitosis ((p=0.003); FIG. 8B). Thus, these findings support that hMSCs/hCSCs interactions are capable of inactivation both pRb and ARF facilitating transient amplifying cell and cardiomyocyte completion of the cell cycle.

pRb$^{Ser608}$ and ARF Correlate with Scar Regression

Lastly, to determine whether pRb$^{Ser608}$ activity reflects myocardial regeneration at the whole organ level, the prediction that levels of pRb$^{Ser608+}$ cardiomyocytes and CPCs correlated with cardiac MRI-based changes in scar size was tested. Indeed, the levels of pRb$^{Ser608+}$ Gata4$^+$ CPCs within the infarct zone correlated with the reduction in scar size in response to cell therapy (FIG. 4). In contrast, the levels of pRb$^{Ser608+}$ cardiomyocytes did not correlate with myocardial scar reduction (FIG. 4). However, pRb$^{Ser608+}$/ARF-negative myocytes within the infarct and the border zones did correlate with the % of scar size reduction (FIG. 4). Thus, these findings substantiate that, mammalian cardiac myocytes have the capacity for regenerative competence.

Discussion

Retinoblastoma is a tumor suppressor widely expressed in adult mammalian tissues and in stem cell niches that regulates cell-cycle activity (Walkley C R, et al. Cell 2007 June 15; 129(6):1081-95; Calo E, eta al. Nature 2010 August 26; 466(7310):1110-4; Burke J R, et al. Genes Dev 2012 June 1; 26(11):1156-66). In invertebrates and in regenerating tissues, pRb is inactivated alone and in combination with a parallel pathway that also suppresses cell-cycle activity, the ARF (Conkrite K, et al. J Clin Invest 2012 May 1; 122(5): 1726-33; Bettencourt-Dias M, et al. J Cell Sci 2003 October 1; 116 (Pt 19):4001-9; Pajcini K V, et al. Cell Stem Cell 2010 August 6; 7(2):198-213). Given the growing awareness that successful cardiac regeneration in response to cell therapy involves endogenous regenerative pathways, the hypothesis was tested that cell therapy with appropriate cells leads to combined inactivation of pRb and ARF in host precursor, transient amplifying, and fully formed myocytes. Together, the data presented here support a key role for this dual inactivation in adult mammalian cardiac tissues. Indeed the presence of precursors with dual inactivation predicted the degree of myocardial recovery post stem cell injection. These effects were mediated by a coordinated action of a stromal cell and a c-kit$^+$ progenitor cell. These findings have important implications for the elucidation of the pathways governing tissue regeneration in adult mammals as well as for the design and implementation of optimal cell-based therapeutic strategies.

Our studies in a pig model of myocardial infarction have shown that transplantation of a combination of bone marrow-derived mesenchymal stem cells (MSCs) and cKit$^+$ cardiac progenitors (CSCs) results in a significant reduction in scar size and improvement in heart function compared to animals not receiving the stem cell therapy. These improvements are accompanied by, and correlate to, a significant increase in the detection frequency of a population of small, mononucleated cardiac myocytes in mitosis. Immunophenotypic analysis with confocal microscopy revealed that, compared to the non-mitotically dividing cardiomyocytes, these small cardiomyocytes in mitosis exhibit hyperphosphorylation in Rb at Serine 608 (Rb$^{Ser608+}$), and lack expression of ARF. In contrast, non-dividing cardiomyocytes exhibit strong expression of ARF, and an underphosphorylated state of Rb. We also detected a large pool of Rb$^{Ser608+}$ cardiomyocytes within and around the infarct scar zone which were not in mitosis. Importantly, these non-dividing Rb$^{Ser608+}$ cardiomyocytes strongly expressed ARF. Furthermore, animals receiving the stem cell therapy present a significant increase in the detection frequency of Gata$^+$ myocardial progenitors which are also Rb$^{Ser608+}$. Collectively, these data suggest that Rb activity underlies the mechanisms of cardiomyogenesis in mammals and that the cardiogenic activity of Rb might be regulated by the cyclin-dependent kinase inhibitor, ARF.

Example 2: Rb Knock-Down Enhances Cardiomyocyte Differentiation

To further explore the role of Rb in cardiomyogenis in in vitro models, human embryonic (hESCs) and induced-pluripotent (hIPSCs) stem cells, were used. Protocols were established to guide their in vitro differentiation into spontaneously beating human cardiomyocytes. In a preliminary set of experiments, gene-expression analysis revealed that induction of cardiogenic program overlaps with a sharp induction in the expression of both Rb and ARF (FIG. 11). These findings are in complete accordance with the hypothesis and in vivo studies in pigs (disclosed in Example 1) which show that Rb activity underlies the mechanisms of cardiomyogenesis in mammals and that the cardiogenic activity of Rb might be regulated by the cyclin-dependent kinase inhibitor, ARF. To gain further insights on the role of Rb in cardiogenesis, transgenic line of hESCs were obtained, in which an shRNA against Rb was stably transduced using a tetracycline-inducible GFP-expressing lentiviral vector (pSLIK). This system allowed to conditionally knockdown Rb in hESCs by the addition of doxycycline in the culture medium, and observe the fate of the affected cell populations by the expression of GFP. Preliminary results demonstrated that addition of doxycycline was accompanied by strong expression of GFP (FIG. 12 A, B) as measured by fluorescent microscopy, and a ~50% reduction in the expression levels of Rb compared to control.

To test the role of Rb on differentiation of myocardial progenitors to human cardiomyocytes, hESCs were subjected to cardiac differentiation protocol. Notably, under this protocol, development of spontaneously contracting embryoid bodies were seen within 7 days after embryoid body formation (EB-day 7). Accordingly, addition of doxocycline was initiated from EB-day 5 to EB-day 8, in order to knockout RB1 in cardiac progenitors prior to their differentiation into beating cardiomyocytes. Quantification of beating embryoid bodies illustrated that, although the numbers of beating EBs on day 8 were similar between the RB1-knockdown and control groups (FIG. 13A), by EB-day 10, the percentage of beating embryoid bodies in the RB1-knockdown groups were 44.6±3.8% compared to 19.0±3.3% in the control group (p=0.0002, one-way ANOVA). Gene-expression analysis of Rb revealed a reduced expression Rb in dox-treated EBs, when compared to the control group (FIG. 13 C). Importantly, fluorescence microscopy illustrated that 100% of the beating EBs in the RB1-knockdown group were GFP+, illustrating that RB1 shRNA was strongly expressed during their differentiation into cardiomyocytes (FIG. 13B). Further, gene-expression analysis of day 10 EBs revealed that Rb knockdown significantly enhanced the transcriptional activities of the cardiac lineage-specific markers GATA4, Isl1 and cardiac troponin I (TnnI) when compared to control (FIG. 14), supporting the role of Rb as a regulator of human cardiomyocyte genesis. Importantly, these changes were accompanied by a significant increase in the expression of CDK4, CDK6, E2F2 and E2F3 (FIG. 15) suggesting that Rb operated through a CDK4/6 and E2F-related pathways. In addition, enhanced expression of the CDK inhibitors CDKN1b ($p21^{kip1}$), CDKN1c ($p57^{kip2}$), CDKN2a (ARF), CDKN2b ($p15^{Ink4b}$), CDKN2c ($p18^{Ink4c}$) and CDKN3 were also recorded (FIG. 16). Furthermore, although knockdown of Rb triggered a significant increase in the transcriptional activity of p107 and p130 (FIG. 16), their activity was not sufficient to suppress cardiogenesis, supporting the hypothesis that differentiation of human cardiac progenitors to cardiomyocytes is regulated by Rb and not p107 and p130.

What is claimed is:

1. A method of isolating cardiac progenitor cells from a population of cardiac cells, the method comprising:
   identifying the cardiac progenitor cells in the population as cells comprising phosphorylated retinoblastoma protein; and
   isolating the identified cardiac progenitor cells.

2. The method of claim 1, wherein the identifying comprises contacting the population of cardiac cells with an agent that detects phosphorylated Rb or hyperphosphorylated Rb.

3. The method of claim 2, wherein the agent binds to Rb phosphorylated at position Ser 608 of Rb.

4. The method of claim 1, further comprising administering the isolated cardiac progenitor cells to a subject in need of such administration.

5. The method of claim 4, wherein the subject has a heart disease.

6. The method of claim 1, wherein the isolated cardiac progenitor cells are positive for Gata4 (Gata4+) and/or negative for ARF (ARF−).

7. The method of claim 1, wherein identifying comprises identifying the cardiac progenitor cells using fluorescence assisted cell sorter (FACS), laser scanning cytometry, fluorescent microscopy, RT-PCR, DNA hybridization, fluorescence in situ hybridization, mass spectroscopy, microarray analysis, immunohistochemistry analysis, or any combination thereof.

8. A method of treating a heart disease in a subject in need thereof comprising administering a therapeutically effective amount of isolated cardiac progenitor cells, wherein the cardiac progenitor cells are isolated according to a method comprising:
   identifying the cardiac progenitor cells in a population as cells comprising phosphorylated retinoblastoma protein; and
   isolating the identified cardiac progenitor cells.

9. The method of claim 8, wherein the isolated cells are positive for Gata4 (Gata4+) and/or negative for ARF (ARF−).

10. The method of claim 8, wherein the heart disease is cardiovascular disease, cardiomyopathy, myocardial stunning, peripheral vascular disease, intermittent claudication, tachycardia, ischemia-reperfusion, myocardial infarction, acute renal failure, stroke, hypotension, embolism, thromboembolism (blood clot), sickle cell disease, localized pressure to extremities to the body, tumors, and combinations thereof.

11. A method of isolating cardiac progenitor cells from a population of cardiac cells, the method comprising:
   identifying the cardiac progenitor cells in the population as cells that are positive for phospho-Rb$^{pos}$ or Gata4, and/or negative for ARF, or any combination thereof; and
   isolating the identified cardiac progenitor cells.

12. The method of claim 11, wherein the cells that are:
   positive for phospho-Rb$^{pos}$ and Gata4 are identified as cardiac progenitor cells;
   positive for phospho-Rb$^{pos}$ and negative for ARF are identified as cardiac progenitor cells;
   are positive for Gata4 and negative for ARF are identified as cardiac progenitor cells; or
   positive for at phospho-Rb$^{pos}$ and Gata4, and negative for ARF are identified as cardiac progenitor cells.

13. The method of claim 11, wherein the identified cardiac progenitor cells are N-cadherin$^{pos}$, connexin-43$^{pos}$, Isl1$^{pos}$, Wt1$^{pos}$, CDK2$^{pos}$, CDK4$^{pos}$, CDK6$^{pos}$, E2F$^{pos}$, phospho-p107$^{pos}$, phospho-p130$^{pos}$, CCNA$^{pos}$, CCND1$^{pos}$, CCND2$^{pos}$, CCND3$^{pos}$, CCNE$^{pos}$, c-kit$^{pos}$, CD3$^{neg}$, CD14$^{neg}$, CD68$^{neg}$, Nkx2.5$^{pos}$, MITF$^{pos}$, MEF2c$^{pos}$, or any combination thereof.

14. The method of claim 11, wherein the method further comprises identifying cells that are N-cadherin$^{pos}$, connexin-43$^{pos}$, Isl1$^{pos}$, Wt1$^{pos}$, CDK2$^{pos}$, CDK4$^{pos}$, CDK6$^{pos}$, E2F$^{pos}$, phospho-p107$^{pos}$, phospho-p130$^{pos}$, CCNA$^{pos}$, CCND1$^{pos}$, CCND2$^{pos}$, CCND3$^{pos}$, CCNE$^{pos}$, c-kit$^{pos}$, CD3$^{neg}$, CD14$^{neg}$, CD68$^{neg}$, Nkx2.5$^{pos}$, MITF$^{pos}$, MEF2c$^{pos}$, or any combination thereof prior to isolating the identified cardiac progenitor cells.

* * * * *